US008921280B2

(12) United States Patent
Cho

(10) Patent No.: US 8,921,280 B2
(45) Date of Patent: *Dec. 30, 2014

(54) INTEGRATED BIO-CHIP AND METHOD OF FABRICATING THE INTEGRATED BIO-CHIP

(75) Inventor: Seong-ho Cho, Gwacheon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1205 days.

This patent is subject to a terminal disclaimer.

(21) Appl. No.: 12/704,236

(22) Filed: Feb. 11, 2010

(65) Prior Publication Data

US 2010/0204064 A1    Aug. 12, 2010

(30) Foreign Application Priority Data

Feb. 11, 2009  (KR) .................. 10-2009-0011211
Feb. 11, 2009  (KR) .................. 10-2009-0011212
Feb. 11, 2009  (KR) .................. 10-2009-0011213
Feb. 11, 2009  (KR) .................. 10-2009-0011216

(51) Int. Cl.
*C40B 60/12*   (2006.01)
*G01N 21/64*   (2006.01)

(52) U.S. Cl.
CPC ................. *G01N 21/6454* (2013.01)
USPC ........................................ 506/17

(58) Field of Classification Search
None
See application file for complete search history.

(56) References Cited

U.S. PATENT DOCUMENTS 6,023,540 A * 2/2000 Walt et al. ............ 385/12
6,493,114 B1 * 12/2002 Liu .................... 358/509
6,667,159 B1 * 12/2003 Walt et al. ............ 435/7.32
7,075,104 B2   7/2006 Faris
7,427,803 B2   9/2008 Chao et al.
2003/0092034 A1 * 5/2003 Cooper et al. .......... 435/6
2004/0101861 A1   5/2004 Little et al.
2004/0234417 A1  11/2004 Schienle et al.
2005/0157301 A1   7/2005 Chediak et al.
2006/0084069 A1   4/2006 Chan et al.
2007/0279631 A1  12/2007 Yershov
2008/0081769 A1   4/2008 Hassibi
2008/0305481 A1 * 12/2008 Whitman et al. ........ 435/6

FOREIGN PATENT DOCUMENTS

EP    1255980 B1    7/2008
KR    1020040009185 A    1/2004
KR    1020050008148 A    1/2005
KR    1020060013504 A    2/2006

(Continued)

OTHER PUBLICATIONS

Extended European Search Report issued by the European Patent Office in Application No. 10153311.5 on May 7, 2012.

*Primary Examiner* — Christian Boesen
(74) *Attorney, Agent, or Firm* — Leydig, Voit & Mayer, Ltd.

(57) ABSTRACT

An integrated bio-chip includes; a sample detection portion including at least one light receiving device which detects fluorescent light emitted from at least one sample, a light transfer portion disposed on a light incident surface of the sample detection portion, and which includes at least one excitation light absorbing waveguide which absorbs an excitation light and transmits the fluorescent light emitted from the at least one sample, and a sample reaction portion disposed adjacent to an incident end of the at least one excitation light absorbing waveguide, and including at least one reaction region on which the at least one sample is attached, wherein the sample detection portion, the light transfer portion, and the sample reaction portion are integrally coupled to each other as a single component.

37 Claims, 35 Drawing Sheets

(56) References Cited

FOREIGN PATENT DOCUMENTS

| KR | 100800161 B1 | 1/2008 |
| KR | 100801448 B1 | 1/2008 |
| KR | 100825087 B1 | 4/2008 |
| WO | WO 01/03833 A1 | 1/2001 |

\* cited by examiner

INTEGRATED BIO-CHIP AND METHOD OF FABRICATING THE INTEGRATED BIO-CHIP

CROSS-REFERENCE TO RELATED APPLICATIONS

This application claims priority to Korean Patent Application No. 10-2009-0011211, filed on Feb. 11, 2009, Korean Patent Application No. 10-2009-0011212, filed on Feb. 11, 2009, Korean Patent Application No. 10-2009-0011213, filed on Feb. 11, 2009 and Korean Patent Application No. 10-2009-0011216, filed on Feb. 11, 2009, and all the benefits accruing therefrom under 35 U.S.C. §119, the contents of which in their entirety are herein incorporated by reference.

BACKGROUND

1. Field

The present disclosure relates to integrated bio-chips and methods of fabricating the same, and more particularly, to integrated bio-chips used for spectroscopically detecting a sample and methods of fabricating the integrated bio-chips.

2. Description of the Related Art

Bio-chips typically have a structure in which very tiny, e.g., microscopic, cells are arranged on a substrate in micro-units in a matrix shape, wherein each of the cells includes biogenic organic materials such as nucleotide and/or protein. Bio-materials fixed on the substrate of the bio-chip operate as biological receptors for target bio-materials.

Bio-chips detect the target bio-materials via interaction between the target bio-materials and the bio-materials which are fixed on the substrate; the various interactions may include a hybridization reaction of a nucleotide or an antigen-antibody interaction. The bio-chips may be used to research functions of genes, to search for illness-related genes, to analyze gene expression, to analyze protein distribution by detecting the bio-materials such as nucleotide or protein having a specific sequence or various other similar uses.

The interaction between the bio-materials may be detected using a fluorescence detection method. The fluorescence detection method is a spectroscopic method of detecting fluorescent images by irradiating a predetermined excitation light on fluorescent materials tagged on the bio-materials, e.g., tagged on the target bio-materials. The detection of the fluorescent images is made using an optical scanning apparatus such as a charge-coupled device ("CCD") scanner or a complementary metal oxide semiconductor ("CMOS") Image Sensor ("CIS") scanner.

The fluorescence obtained by irradiating the predetermined excitation light onto the fluorescent material tagged on the bio-materials is much weaker than the excitation light used for irradiation of the fluorescent material, and thus may obscure fluorescence detection. Therefore, an apparatus or method which could reduce the unwanted obscuration effects of the excitation light would be advantageous. In addition, current detection apparatuses use a scanner-type photodetector that is large, complex, and expensive, and thus, a compact bio-chip and a detection apparatus having the same would be an improvement.

SUMMARY

Provided are compact bio-chips having integrated function of reacting and detecting samples, and methods of fabricating the bio-chips.

Additional aspects will be set forth in part in the description which follows and, in part, will be apparent from the description, or may be learned by practice of the presented embodiments.

According to an aspect of the present disclosure, an integrated bio-chip includes: a sample detection portion including at least one light receiving device which detects fluorescent light emitted from at least one sample, a light transfer portion disposed on a light incident surface of the sample detection portion, and which includes at least one excitation light absorbing waveguide which absorbs an excitation light and transmits the fluorescent light emitted from the at least one sample, and a sample reaction portion disposed adjacent to an incident end of the at least one excitation light absorbing waveguide, and including at least one reaction region on which the at least one sample is attached, wherein the sample detection portion, the light transfer portion, and the sample reaction portion are integrally coupled to each other as a single component.

In one embodiment, the light transfer portion may include a light blocking portion surrounding each of the at least one excitation light absorbing waveguide and blocking the excitation light and the fluorescent light.

In one embodiment, the light blocking portion may be formed of a black material absorbing the excitation light and the fluorescent light.

In one embodiment, at least one excitation light absorbing waveguide may have a refractive index that is greater than a refractive index of the light blocking portion.

In one embodiment, the excitation light absorbing waveguide may include a color filter core that transmits the fluorescent light emitted from the samples and absorbs the excitation light that excites the samples.

In one embodiment, the color filter core may have a refractive index that is greater than a refractive index of a substrate surrounding the color filter core.

In one embodiment, the excitation light absorbing waveguide may further include a clad layer that is disposed on a circumference of the color filter core and has a refractive index that is lower than the refractive index of the color filter core.

In one embodiment, the integrated bio-chip may further include a micro lens disposed on an optical path between the at least one reaction region and the light receiving device for condensing the fluorescent light.

In one embodiment, the integrated bio-chip may further include a fluorescence anti-reflection layer disposed on the at least one reaction regions for transmitting the fluorescent light emitted from the samples.

In one embodiment, the sample detection portion may be a photo multiplier tube ("PMT"), a charge coupled device ("CCD"), or a complementary metal oxide semiconductor ("CMOS") image sensor ("CIS").

In one embodiment, the sample detection portion may include an image sensor of a front illumination type. The sample detection portion may include an image sensor of a back illumination type.

In one embodiment, the light receiving device of the sample detection portion may correspond to the at least one reaction region in one-to-one correspondence or one-to-many correspondence.

In one embodiment, the integrated bio-chip may further include a frame on which the sample reaction portion, the light transfer portion, and the sample detection portion are mounted.

In one embodiment, the integrated bio-chip may further include a cover glass disposed apart from the sample reaction portion for protecting the sample reaction portion.

In one embodiment, the cover glass may include a fluorescence reflection layer for reflecting the fluorescent light emitted from the samples on an inner surface of the cover glass.

In one embodiment, the fluorescence reflection layer may be a dichroic mirror reflecting a wavelength band of the fluorescent light or a band reject filter that shields a wavelength band of the fluorescent light.

In one embodiment, the fluorescence reflection layer may pass a wavelength band of the excitation light.

In one embodiment, at least one micro mirror for condensing and reflecting the fluorescent light emitted from the samples may be disposed on an inner surface of the cover glass.

In one embodiment, the micro mirror may be concave so as to reflect the incident fluorescent light while condensing the fluorescent light.

In one embodiment, the micro mirror may correspond to the reaction region of the sample reaction portion in one-to-one correspondence or in one-to-many correspondence.

In one embodiment, an anti-excitation light reflection layer for preventing the excitation light from being reflected may be formed on an outer surface of the cover glass.

According to another aspect of the present disclosure, a method of fabricating an integrated bio-chip, the method includes; preparing a sample detection portion including at least one light receiving device, providing a light transfer portion having at least one excitation light absorbing waveguide on a light incident surface of the sample detection portion and providing a sample reaction portion including at least one reaction region on which at least one sample is attached on an upper surface of the light transfer portion.

In one embodiment, the forming of the light transfer portion may include: applying an excitation light absorbing material that absorbs the excitation light and transmits the fluorescent light on an upper surface of the sample detection portion; forming the excitation light absorbing waveguide by forming at least one trench in the applied excitation light absorbing material so as to expose the upper surface of the sample detection portion except for the portion where the light receiving device is located; and filling a black material that absorbs the excitation light and the fluorescent light in the trench to form a light blocking portion.

In one embodiment, the forming of the light transfer portion may include: applying a black material that absorbs the excitation light and the fluorescent light on an upper surface of the sample detection portion; forming at least one trench in the applied black material so as to expose upper portion of the sample detection portion, where the light receiving device is located, to form a light blocking portion; and filling an excitation light absorbing material that absorbs the excitation light and transmits the fluorescent light to form the excitation light absorbing waveguide.

In one embodiment, the forming of the light transfer portion may include: forming at least one penetration hole in the substrate; filling a color filter material in the at least one penetration hole to from a color filter core; and bonding the substrate to the light incident surface of the sample detection portion.

In one embodiment, the forming of the light transfer portion may include forming a clad layer on an inner wall of the at least one penetration hole before forming the color filter core.

In one embodiment, the forming of the light transfer portion may further include forming at least one micro lens on the at least one excitation light absorbing waveguide.

In one embodiment, the sample detection portion may include a PMT, a CCD or a CIS.

In one embodiment, the forming of the sample detection portion may include preparing a pre-polished sample detection portion including a photodiode portion including photodiodes and a distribution line portion formed on a surface of the photodiode portion; and bonding a dummy substrate on a surface of the pre-polished sample detection portion, where the distribution line portion is disposed, and polishing the opposite surface of the pre-polished sample detection portion to a predetermined depth; wherein the light transfer portion is disposed on the surface of the sample detection portion where the photodiode portion is disposed.

In one embodiment, the light receiving device of the sample detection portion may correspond to the at least one excitation light absorbing waveguide in one-to-one correspondence or one-to-many correspondence.

In one embodiment, the bonding of the light transfer portion to the sample detection portion may be performed in a wafer unit or a single chip unit.

In one embodiment, the method may further include disposing a cover glass at a predetermined distance from the sample reaction portion.

In one embodiment, the forming of the cover glass may include: forming a fluorescence reflection layer that reflects the fluorescent light emitted from the samples on an inner surface of the cover glass.

In one embodiment, the forming of the cover glass may include forming at least one micro mirror that condenses and reflects the fluorescent light emitted from the samples on the inner surface of the cover glass.

In one embodiment, the forming of the at least one micro mirror may include forming the micro mirror to be concave so as to reflect the fluorescent light while condensing the incident fluorescent light.

In one embodiment, the forming of the at least one micro mirror may include forming the micro mirror to correspond to the reaction region of the sample reaction portion in one-to-one or one-to-many correspondence.

In one embodiment, the forming of the cover glass may further include an anti-excitation light reflection layer that prevents the excitation light from being reflected on an outer surface of the cover glass.

According to another aspect of the present disclosure, a bio-material detecting apparatus using an integrated bio-chip, which includes; a sample detection portion including at least one light receiving device which detects fluorescent light; a light transfer portion disposed on a light incident surface of the sample detection portion, and which includes at least one excitation light absorbing waveguide which absorbs an excitation light for exciting samples and which transmits a fluorescent light emitted from the at least one sample; and a sample reaction portion disposed on a portion corresponding to an incident end of the at least one excitation light absorbing waveguide in the light transfer portion, and including at least one reaction region on which the at least one sample is attached, wherein the sample detection portion, the light transfer portion, and the sample reaction portion are integrally coupled to each other, the bio-material detecting apparatus including: an illumination optics which illuminates excitation light to the integrated bio-chip, and a stage on which the integrated bio-chip is detachably installed.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
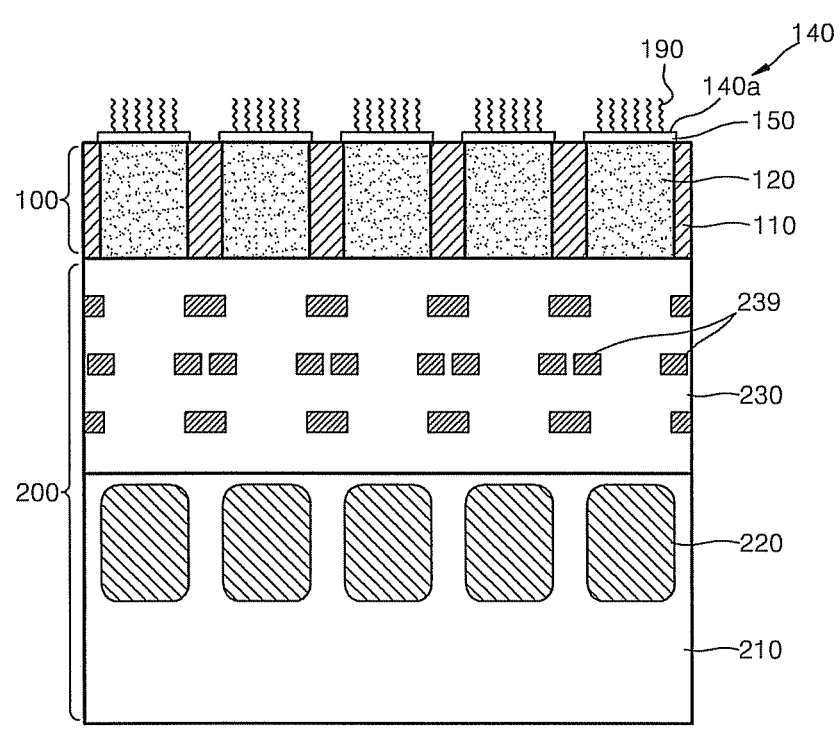
FIG. 1 is a schematic cross-sectional view of an embodiment of an integrated bio-chip according to the present disclosure.

Embodiments now will be described more fully hereinafter with reference to the accompanying drawings, in which embodiments are shown. These embodiments may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the disclosure.

All methods described herein can be performed in a suitable order unless otherwise indicated herein or otherwise clearly contradicted by context. The use of any and all examples, or exemplary language (e.g., "such as"), is intended merely to better illustrate the disclosure and does not pose a limitation on the scope thereof unless otherwise claimed. No language in the specification should be construed as indicating any non-claimed element as essential to the practice of the embodiments as used herein.

Hereinafter, the embodiments will be described in detail with reference to the accompanying drawings.

FIG. 1 is a schematic cross-sectional view of an embodiment of an integrated bio-chip according to the present disclosure.

Referring to FIG. 1, the integrated bio-chip of the present embodiment includes a sample reaction portion 140 to which samples 190 are attached, a sample detection portion 200 for detecting fluorescence emitted from the samples 190, and a light transfer portion 100 located between the sample reaction portion 140 and the sample detection portion 200. In the present embodiment the sample reaction portion 140, the light transfer portion 100 and the sample detection portion 200 are coupled to each other and integrated as a chip, e.g., the sample reaction portion 140, the light transfer portion 100 and the sample detection portion 200 are integrated as a single, unitary and indivisible component.

The sample reaction portion 140 to which samples 190 are attached is disposed on an upper surface of the light transfer portion 100, and the light transfer portion 100 includes a light blocking portion 110 and a plurality of excitation light absorbing waveguides 120 surrounded by the light blocking portion 110.

In one embodiment, the light blocking portion 110 may be formed of a black material that absorbs both the excitation light exciting the samples 190 and fluorescent light emitted from the samples 190 themselves, and surrounds each of the excitation light absorbing waveguides 120. In one embodiment, the light blocking portion 110 may be formed in a matrix shape.

The excitation light absorbing waveguide 120 forms an optical path that guides the fluorescent light emitted from the samples 190 to the sample detection portion 200 while absorbing the excitation light, e.g., the excitation light absorbing waveguide 120 has an absorbency that is wavelength specific. In general, a wavelength of the fluorescent light is longer than that of the excitation light which excites the fluorescent light, and thus, the excitation light absorbing waveguide 120 is formed of a color filter material that transmits the fluorescent light and absorbs the excitation light. In one embodiment, the color filter material forming the excitation light absorbing waveguide 120 may have a refractive index that is greater than that of the material forming the light blocking portion 110. However, the integrated bio-chip of the present embodiment is not limited thereto. That is, if the refractive index of the color filter material forming the excitation light absorbing waveguide 120 is equal to or smaller than the refractive index of the material forming the light blocking portion 110, the light transfer portion 100 may block the excitation light and transmit the fluorescent light through each of the excitation light absorbing waveguides 120, although there may be a minor loss of light.

A reaction region of the sample reaction portion 140, to which the samples 190 are attached, is disposed on an end portion of the excitation light absorbing waveguide 120, that is, an incident end thereof. In addition, the opposing end portion of the excitation light absorbing waveguide 120, that is, an exit end thereof, contacts the sample detection portion 200. A cross-section of the excitation light absorbing waveguide 120 may have a shape corresponding to a shape of the reaction region 140a, for example, may have a circular or polygonal cross-sectional shape. The reaction regions 140a may be separated from each other in a two-dimensional structure, e.g., a matrix pattern, and accordingly, the excitation light absorbing waveguides 120 may be also separate from each other. However, embodiments of the cross-section or arrangement structure of the excitation light absorbing waveguides 120 is not limited to the above example.

In one embodiment, the light blocking portion 110 and the excitation light absorbing waveguides 120 may be formed in the same layer. Thickness of the light blocking portion 110 and the excitation light absorbing waveguide 120 may be designed according to an efficiency to which the excitation light absorbing waveguide material absorbs excitation light so as to sufficiently blocking the excitation light. For example, in one embodiment the light blocking portion 110 and the excitation light absorbing waveguide 120 may be formed to a thickness of about a few μm to tens of μm or more.

A fluorescence anti-reflection layer 150 may be further disposed on the incident end of the excitation light absorbing waveguide 120. The fluorescence anti-reflection layer 150 prevents the fluorescent light emitted from the samples 190 from being reflected at the incident end of the excitation light absorbing waveguide 120 so as to improve a fluorescence detecting efficiency of the device. In one embodiment, the fluorescence anti-reflection layer 150 may be formed to completely cover the end portion of the excitation light absorbing waveguide 120. In another embodiment, the fluorescence anti-reflection layer 150 may be formed to completely cover the light transfer portion 100. In one embodiment, the fluorescence anti-reflection layer 150 may be formed of a material chosen to have an affinity to samples 190 or a solution in which the samples 190 are dispersed so that the samples 190 may be attached thereto.

The sample reaction portion 140 includes a plurality of reaction regions 140a to which the samples 190 may be attached. The plurality of reaction regions 140a are formed on an upper surface of the light transfer portion 100, and may correspond to the excitation light absorbing waveguides 120 in one-to-one correspondence. The plurality of reaction regions 140*a* are areas to which the samples 190 are attached. For example, if the fluorescence anti-reflection layer 150 is formed of a material having an affinity with respect to the samples 190, regions where the fluorescence anti-reflection layer 150 is formed become the reaction regions 140*a*. In one embodiment, the fluorescence anti-reflection layer 150 may be separately formed under the reaction regions 140*a*. However, embodiments also include configurations wherein the fluorescence anti-reflection layer 150 may be omitted. When the fluorescence anti-reflection layer 150 is omitted, surfaces of the reaction regions 140*a* may be treated to have affinity with respect to the samples 190 or the solution in which the samples 190 are dispersed. The surface treatment may vary depending on the samples 190 that are to be detected. Embodiments include configurations wherein the reaction regions 140*a* may be locally oxidized, or doped with an oxide or a hydrophilic material so as to have a hydrophilic property. However, the surface treatment is not limited to the above example. An ion exchange surface, an immobilized metal surface, or other various surface treatments may be used in order to provide affinity to the surface according to the samples 190. The plurality of reaction regions 140*a* may be areas on which probe bio-materials functioning as biological receptors of target bio-materials are fixed. In one embodiment, the probe bio-material may be fixed on the sample reaction portion 140 through a semiconductor process.

The plurality of reaction regions 140*a* are separated from each other, and each of the reaction regions 140*a* may have a diameter ranging from the sub μm scale to about a few μm. In addition, in one embodiment the plurality of reaction regions 140*a* may be arranged in two-dimensional structure such as a matrix. Embodiments include configurations wherein the reaction region 140*a* may have a circular shape, or a polygonal shape such as a rectangle. In the integrated bio-chip of the present embodiment, the plurality of reaction regions 140*a* all include the same type of probe biomolecules. For example, if the integrated bio-chip of the present embodiment is used as a deoxyribonucleic acid ("DNA") chip, each of the reaction regions 140*a* is a minimum unit on which a plurality of probe nucleotides of the same kind are attached, such that each reaction region 140*a* may individually test for a different target nucleotide, and is a minimum pixel of a fluorescent image that is obtained when the excitation light is irradiated onto the DNA chip for detecting target nucleotides. Alternatively, each reaction region 140*a* may have the same probe nucleotide as every other reaction region 140*a* in order to provide redundancy and sensitivity.

The samples 190 attached to the integrated bio-chip of the present embodiment may be detected by a fluorescence detection method. The samples may be, for example, bio-materials such as nucleotide having fluorescent tags attached thereto. The bio-material attached to the reaction region 140*a* may be a probe bio-material or a target bio-material that is combined with the probe bio-material, e.g., through hybridization. The probe bio-materials are molecules that may interact with the target bio-materials, for example, a nucleotide molecule having a sequence that is complementary to the nucleotide molecule that is to be detected. Alternatively, the target bio-materials may be biological organic materials such as animal enzymes, protein, antibodies, nucleotides, microorganisms, cells and organs of animals and/or plants, etc. In an embodiment wherein the bio-chip is a DNA chip, probe nucleotides of a plurality of kinds are respectively attached to predetermined reaction regions 140*a* in single stranded shapes as the probe bio-materials. When the probe nucleotides having sequences complementary to those of the target nucleotides (for example, mRNA) are combined with the target nucleotides via a hybridization reaction and the combined nucleotides are exposed to an excitation light, the nucleotide emits the fluorescent light due to the fluorescent material tagged thereon. Locations of the probe nucleotides on the predetermined reaction regions 140*a* are determined in advance, and thus, the existence of the plurality of target nucleotides may be determined from two-dimensional fluorescent images of the array of reaction regions 140*a*.

The sample detection portion 200 is located under the light transfer portion 100, and detects the fluorescent light guided by the excitation light absorbing waveguide 120. The sample detection portion 200 includes a photodiode portion 210 in which a plurality of photodiodes 220 are formed and a distribution line portion 230 including a control circuit for processing signals and a plurality of distribution lines 239. However, the photodiode 220 is only an example of a light receiving device, and alternative embodiments may include alternative light receiving devices. The sample detection portion 200 may further include a signal processor (not shown) for processing signals of detected fluorescent images. According to the present embodiment, the fluorescent light from the combined samples and probes is incident on the distribution line portion 230 prior to entering the photodiode portion 210. The photodiodes 220 may be arranged to correspond to end portions of the excitation light absorbing waveguides 12, which emit the fluorescent light, in one-to-one correspondence or one-to-many correspondence. The sample detection portion 200 may be, for example, a substrate on which an image sensor such as a photo multiplier tube ("PMT"), a charge coupled device ("CCD") or a complementary metal oxide semiconductor ("CMOS") image sensor ("CIS") is disposed. For example, in a case of the CIS, a CMOS circuit may be formed on a surface of the photodiode portion 210. The sample detection portion 200 may further include a signal processor (not shown) for processing the detected fluorescent light. The use and structure of an image sensor is well known in the art, and thus, further detailed descriptions about the image sensor are not provided here.

Figure 2:
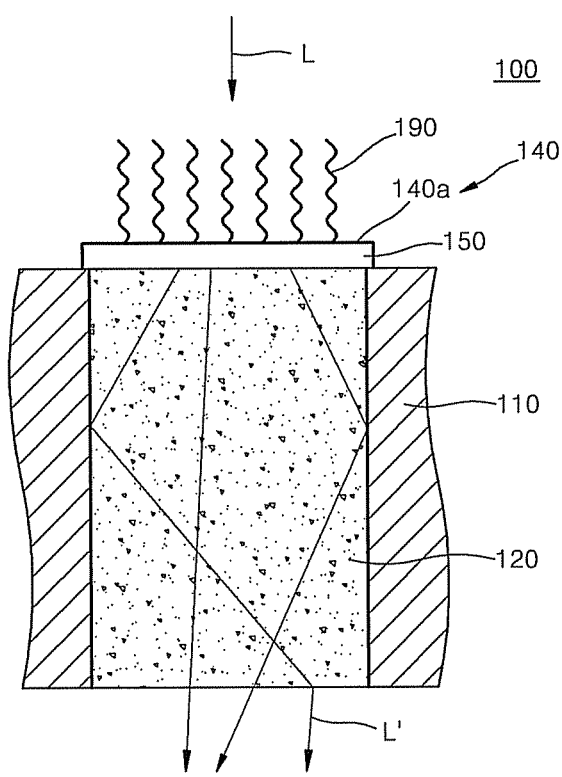
FIG. 2 is an enlarged partial cross-sectional view of an excited light absorbing waveguide in a sample reaction portion as shown in FIG. 1.

FIG. 2 is a schematic diagram of an optical path of the fluorescent light emitted from the sample 190 in present embodiment of the integrated bio-chip.

Referring to FIG. 2, the fluorescent light L' is generated due to the excitation light L, and the excitation light L and the fluorescent light L' proceeding in a downward direction are incident upon the fluorescence anti-reflection layer 150. The excitation light absorbing waveguide 120 absorbs the excitation light L and transmits the fluorescent light L'. Therefore, between the excitation light L and the fluorescent light L' incident in the fluorescence anti-reflection layer 150, only the fluorescent light L' proceeds toward the sample detection portion (200 of FIG. 1) via the excitation light absorbing waveguide 120. In addition, the light incident in the light blocking portion 110 among the excitation light L and the fluorescent light L' proceeding in a downward direction may be reflected by a surface of the light blocking portion 110, or absorbed by the light blocking portion 110 while being incident upon the light blocking portion 110. Therefore, only the fluorescent light L1' that is guided by the excitation light absorbing waveguide 120 that corresponds to a location of the sample 190 emitting that fluorescent light L' is passed to the sample detection portion 200 through the excitation light absorbing waveguide 120 corresponding to the individual sample 190, and thus, blurring of the fluorescent image caused by the fluorescent light L' emitted from neighboring sample 190 may be prevented. On the other hand, the excitation light L proceeding downward may be reflected by the surface of the light transfer portion 100 or absorbed by the light transfer portion 100 while passing through the light transfer portion 100, and does not leak through the lower portion of the light transfer portion 100.

The excitation light absorbing waveguides 120 may correspond to the reaction regions 140*a* in one-to-one correspondence or in one-to-many correspondence, e.g., there may be one excitation light absorbing waveguide 120 for a plurality of reaction regions 140*a*. Accordingly, the image formed by the fluorescent light emitted from the samples 190 is shown on a surface of the light transfer portion 100 facing the sample detection portion 200. Therefore, the sample detection portion 200 may directly read the fluorescent image emitted from the samples 190 without using a separate optical member. As described above, since the chip directly reads the fluorescent images by itself, the integrated bio-chip of the present embodiment does not need additional detecting optics, and size of a bio-detecting apparatus may be reduced.

Figure 3:
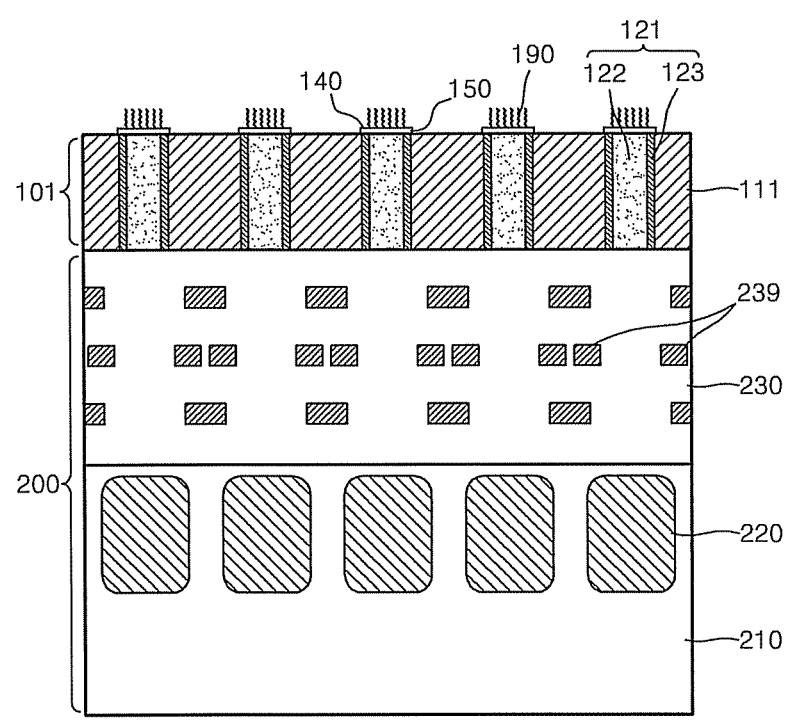
FIG. 3 is a schematic cross-sectional view of another embodiment of an integrated bio-chip according to the present disclosure.

FIG. 3 is a schematic diagram showing another embodiment of an integrated bio-chip according to the present disclosure.

Referring to FIG. 3, the integrated bio-chip includes the sample reaction portion 140 to which samples may be attached, the sample detection portion 200 detecting fluorescent light emitted from the samples, and a light transfer portion 101 located between the sample reaction portion 140 and the sample detection portion 200. The present embodiment of an integrated bio-chip is substantially similar to the previous embodiment of an integrated bio-chip except for the light transfer portion 101.

The light transfer portion 101 of the present embodiment includes a substrate 111 and a plurality of excitation light absorbing waveguides 121 penetrating through the substrate 111.

The substrate 111 may be formed of a material different than the black material as described above. Instead, the substrate 111 may be formed of a material generally used to form a semiconductor substrate, for example, Si, GaAs, or InP substrates, glass, a dielectric material, a metal material, a polymer or other materials having similar characteristics.

In the present embodiment, each of the plurality of excitation light absorbing waveguides 121 have a total reflection waveguide structure including a color filter core 122 and a clad layer 123.

The color filter core 122 is formed of a material that transmits the fluorescent light beam emitted from the sample and absorbs the excitation light used for exciting the sample, and a longitudinal cross-section of the color filter core 122 may be a circle, a polygon or other similar shape. The cross-sectional shape of the color filter core 122 may correspond to the shape of the sample reaction portion 140. In general, a wavelength of the fluorescent light is longer than that of the excitation light, and thus, the color filter core 122 may be formed of a color filter material having a bandpass that is substantially equal to the wavelength band of the fluorescent light. For example, a transparent semiconductor material, polymer, or dielectric material may be dyed using a dye having a wavelength corresponding to the wavelength of the fluorescent light, or the dye having the wavelength of the fluorescent light may be mixed with or dispersed in the transparent semiconductor material, the polymer, or the dielectric material. The dye or pigment used in the color filter is well known in the field of displays or optics, and thus additional detailed descriptions about the dye or the pigment are not provided here.

In the present embodiment, the clad layer 123 is formed of a material having a refractive index that is lower than that of the color filter core 122 so as to totally reflect the fluorescent light incident thereto after passing through the color filter core 122. For example, in one embodiment the clad layer 123 may be formed of an oxide material such as MgF, $SiO_2$ or other material with similar characteristics. The refractive index of the clad layer 123 may be reduced further by adding a dopant. Alternatively, or in addition, the refractive index of the color filter core 122 may be increased by adding a dopant in the color filter core 122.

In one embodiment, the clad layer 123 may have a multi-layered structure wherein the multiple layers have different refractive indexes from each other, or may have a structure wherein the refractive index is gradually changed across a single layer, or may have a structure including a plurality of layers wherein at least one of the layers has a refractive index which gradually changes thereacross. In an embodiment wherein the refractive index of the substrate 111 is smaller than that of the color filter core 122, the clad layer 123 may be omitted and the substrate 111 around the color filter core 122 may function similarly to the clad layer as described above. On the other hand, when the refractive index of the color filter core 122 is gradually changed, for example, when a graded index optical fiber is used, the refractive index may be successively changed at a boundary between the color filter core 122 and the clad layer 123.

Since the fluorescent light L' emitted from the sample due to the excitation light L is non-directional, the fluorescent light L' radiates in substantially all directions. However, most of the fluorescent light is transferred to the sample detection portion 200 through the total reflection in the excitation light absorbing waveguide 121. Thus, loss of the light may be reduced due to the total reflection of the fluorescent light.

Figure 4:
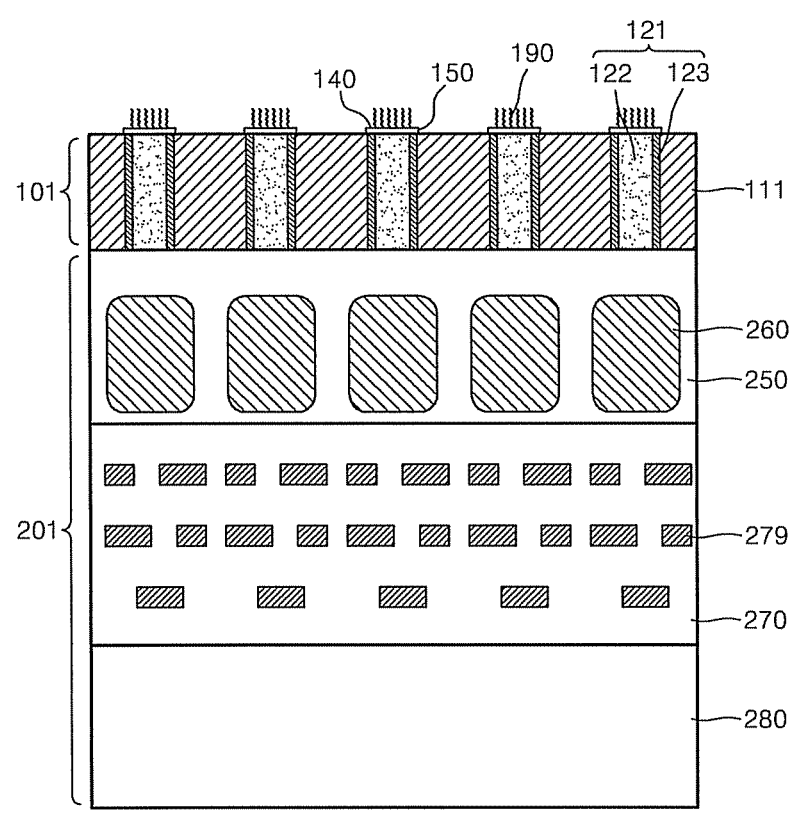
FIG. 4 is a schematic cross-sectional view of another embodiment of an integrated bio-chip according to the present disclosure.

FIG. 4 is a schematic cross-sectional view of another embodiment of an integrated bio-chip according to the present disclosure.

Referring to FIG. 4, the present embodiment of an integrated bio-chip includes the sample reaction portion 140 to which samples may be attached, a sample detection portion 201 which detects fluorescent light emitted from the samples, and a light transfer portion 101 located between the sample reaction portion 140 and the sample detection portion 201. The integrated bio-chip of the present embodiment is substantially similar to the integrated bio-chip of the previous embodiment described with reference to FIG. 3 except for the sample detection portion 201.

The sample detection portion 201 of the present embodiment includes a photodiode portion 250 including a plurality of photo diodes 260, a distribution line portion 270 including a control circuit for processing signals and distribution lines 279, and a dummy substrate 280 supporting the photodiode portion 250 and the distribution line portion 270 thereon. The sample detection portion 201 of the present embodiment is a back illumination type image sensor, that is, the photodiode portion 250 directly contacts the light transfer portion 101 so that the light is directly incident in the photodiode portion 250 without passing through the distribution line portion 270. Embodiments include configurations wherein the sample detection portion 201 may further include a signal processor (not shown) for processing the detected fluorescent light. The sample detection portion 201 may be a substrate on which an image sensor such as a back illumination type CCD or a back illumination type CIS is disposed. The back illumination type image sensor is well known in the art, and thus, additional descriptions about the image sensor are not provided here.

According to the present embodiment, the sample detection portion 201 is formed as the back illumination type image sensor and weak fluorescent light may be efficiently detected. That is, a back surface of the sample detection portion 201, on which the distribution line portion 270 is not disposed, becomes the light incident surface, and thus, elements that interrupt light receiving, for example, the control circuit and the distribution lines 279, may be disposed such that they are out of the optical path of fluorescent light from the sample 190, and the photodiodes 260 may directly receive the fluorescent light from the sample 190 after the fluorescent light travels through the excitation light absorbing waveguides 121. Accordingly, degradation of light sensitivity that may be caused by diffused reflection and difference in refractive indexes when the light passes through the control circuit and the distribution lines in the front illumination type structure may be prevented. In addition, a distance between the light incident surface of the sample detection portion 201 to the photodiodes 260 may be reduced to a few µm or less, and thus the light sensitivity may be improved (a reduction in distance between the light source and the detector is significant in that luminosity of a light source decreases according to the square of distance from the light source), and interference between neighboring pixels may be reduced.

Figure 5:
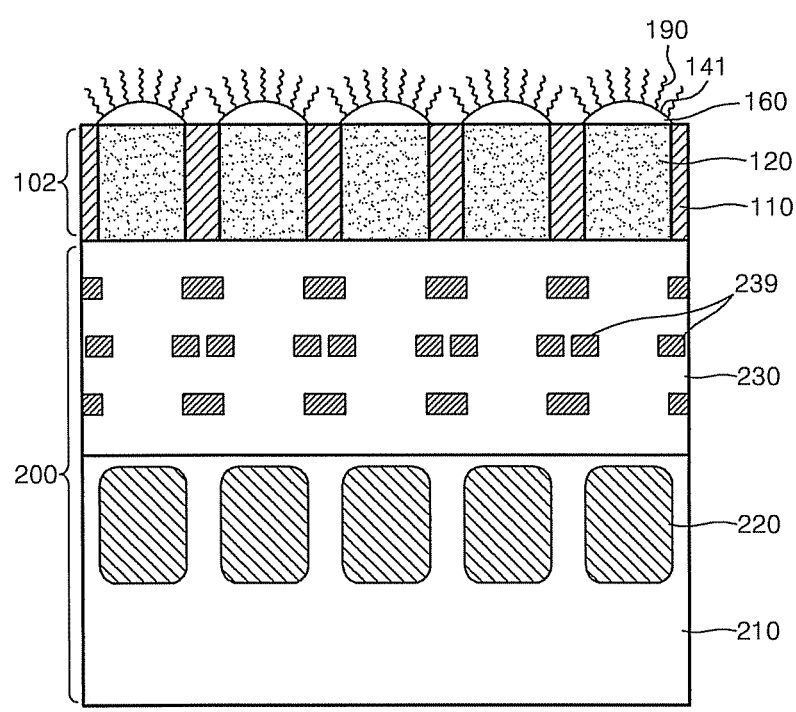
FIG. 5 is a schematic cross-sectional view of another embodiment of an integrated bio-chip according to the present disclosure.

FIG. 5 is a schematic cross-sectional view of another embodiment of an integrated bio-chip according to the present disclosure. Referring to FIG. 5, the present embodiment of an integrated bio-chip includes a sample reaction portion 141, a light transfer portion 102, and the sample detection portion 200. The integrated bio-chip of the present embodiment is substantially similar to the integrated bio-chip described with reference to FIG. 1 except that a micro lens 160 is further disposed on the excitation light absorbing waveguides 120.

The light transfer portion 102 includes the light blocking portion 110, and a plurality of excitation light absorbing waveguides 120 surrounded by the light blocking portion 110, and a plurality of micro lenses 160 disposed on the plurality of excitation light absorbing waveguides 120.

The micro lenses 160 correspond to the light incident ends of the excitation light absorbing waveguides 120 in a one-to-one correspondence. A surface of the micro lens 160 becomes a reaction region 141 to which samples are attached. The surface of the micro lens 160 or the peripheral surface of the micro lens 160 are treated so that the samples are attached only to the surface of the micro lens 160. For example, when the light blocking portion 110 is formed of a material that is not affinitive to the samples or the liquid in which the samples are dispersed, the surface of the micro lens 160 may be treated to have an affinity to the samples or the liquid in which the samples are dispersed. The above surface treatment may vary depending on the samples that are to be detected. For example, in one embodiment the surface of the light blocking portion 110 may be treated to have a hydrophobic property, and the micro lens 160 may be oxidized to have a hydrophilic property, although the present disclosure is not limited thereto.

Embodiments include configurations wherein a fluorescence anti-reflection layer (not shown) is formed on the surface of the micro lens 160 to prevent the loss of fluorescent light on the surface of the micro lens 160. As described above, the fluorescence anti-reflection layer may be formed of a material that is affinitive to the samples or the liquid in which the samples are dispersed. Embodiments include configurations wherein the fluorescence anti-reflection layer is not included.

In the present embodiment, the micro lens 160 has a convex shape, and has a refractive power to condense the fluorescent light emitted from the samples onto the excitation light absorbing waveguides 120. Since the surface of the micro lens 160 is convex, the surface area of the micro lens 160 is wider than the planar surface area of the excitation light absorbing waveguides 120. The surface of the micro lens 160 becomes the reaction region 141 to which the samples are attached, and thus, when the convex micro lens 160 is used in the present embodiment, more samples may be attached than those attached to directly to the planar surface excitation light absorbing waveguides 120 or a fluorescence anti-reflection layer corresponding to the planar surface excitation light absorbing waveguides 120. Therefore, the intensity of the fluorescent light emitted from the samples that are to be detected may increase.

In addition, the fluorescent light incident to the excitation light absorbing waveguide 120 may be transferred only when the fluorescent light satisfies the total reflection conditions in the excitation light absorbing waveguide 120. Therefore, an incident angle of light that is transferred through the excitation light absorbing waveguide 120 is limited. In the present embodiment, since the fluorescent light incident to the excitation light absorbing waveguide 120 is refracted by the micro lens 160, the tilted incident fluorescent light may be transferred while satisfying the total reflection conditions of the excitation light absorbing waveguide 120. Accordingly, much of the fluorescent light emitted from the samples may be transferred through the excitation light absorbing waveguide 120.

In the present embodiment, the micro lens 160 is formed as a convex hemisphere; however, the shape of the micro lens is not limited to the above example. Since the samples such as the target bio-materials typically flows along the surface of the integrated bio-chip while being dispersed in a liquid, the refractive index of the liquid in which the samples are dispersed may be greater than that of the micro lens 160. As described above, in an embodiment wherein the refractive index of the liquid in which the samples are dispersed is relatively greater than that of the micro lens 160, the plurality of micro lenses 160 having concave hemispherical shapes may be formed in the light incident surface of the excitation light absorbing waveguides 120.

In the present embodiment, the micro lenses 160 are formed on a side of the sample reaction portion 141, however, the present disclosure is not limited thereto. For example, the micro lenses 160 may be disposed on a boundary between the light transfer portion 102 and the sample detection portion 200, or may be disposed within the sample detection portion 200.

When the fluorescent light exits the excitation light absorbing waveguide 120 after transferring through the excitation light absorbing waveguide 120, a cross-sectional area of the light flux increases only gradually. A Rayleigh length refers to a length from a point where the cross-sectional area of the light flux is at a minimum to a point where the cross-sectional area of the light flux becomes twice the minimum value. Therefore, a photodiode 220 in the sample detection portion 200 may be disposed apart from the end portions of the excitation light absorbing waveguides 120 at about a Rayleigh length, or less, in order to improve the efficiency of detecting the fluorescent light. Moreover, when a focal length of the micro lens 160 is appropriately designed, the light transfer portion 102 may sufficiently guide the fluorescent light to the photodiode portion 210 without using the waveguide structure. That is, in an embodiment when the focal length of the micro lens 160 is designed appropriately, the fluorescent light is not dispersed, but is condensed on the photodiodes 160 after passing through the light transfer portion 102 and the distribution line portion 230 even when the light blocking portion 110 is formed of the same material as that of the excitation light absorbing waveguide 120.

Figure 6:
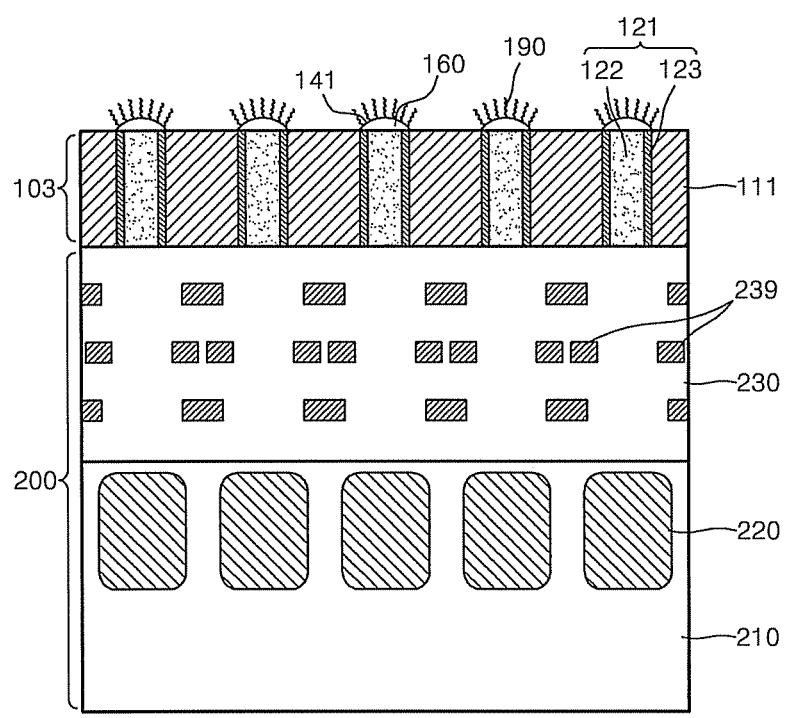
FIG. 6 is a schematic cross-sectional view of another embodiment of an integrated bio-chip according to the present disclosure.

FIG. 6 is a schematic cross-sectional view of another embodiment of an integrated bio-chip according to the present disclosure. Referring to FIG. 6, the integrated bio-chip includes the sample reaction portion 141, the sample detection portion 200 and a light transfer portion 103 located between the sample reaction portion 141 and the sample detection portion 200. The integrated bio-chip of the present embodiment is substantially similar to the embodiment of an integrated bio-chip described with reference to FIG. 3 except for that in the present embodiment the light transfer portion 103 further includes the micro lenses 160.

The light transfer portion 103 includes a substrate 111, a plurality of excitation light absorbing waveguides 121 penetrating through the substrate 111, and a plurality of micro lenses 160 disposed on upper portions of the plurality of excitation light absorbing waveguides 121. Each of the excitation light absorbing waveguides 121 includes the color filter core 122 and the clad layer 123.

The micro lenses 160 correspond to the end portions of the excitation light absorbing waveguides 120 in a one-to-one correspondence. A surface of the micro lens 160 becomes a reaction region to which samples are attached, and a peripheral portion of the micro lens 160 becomes a non-reaction region to which the samples are not attached. The micro lens 160 of the present embodiment are substantially similar to the micro lens described with reference to FIG. 5.

Figure 7:
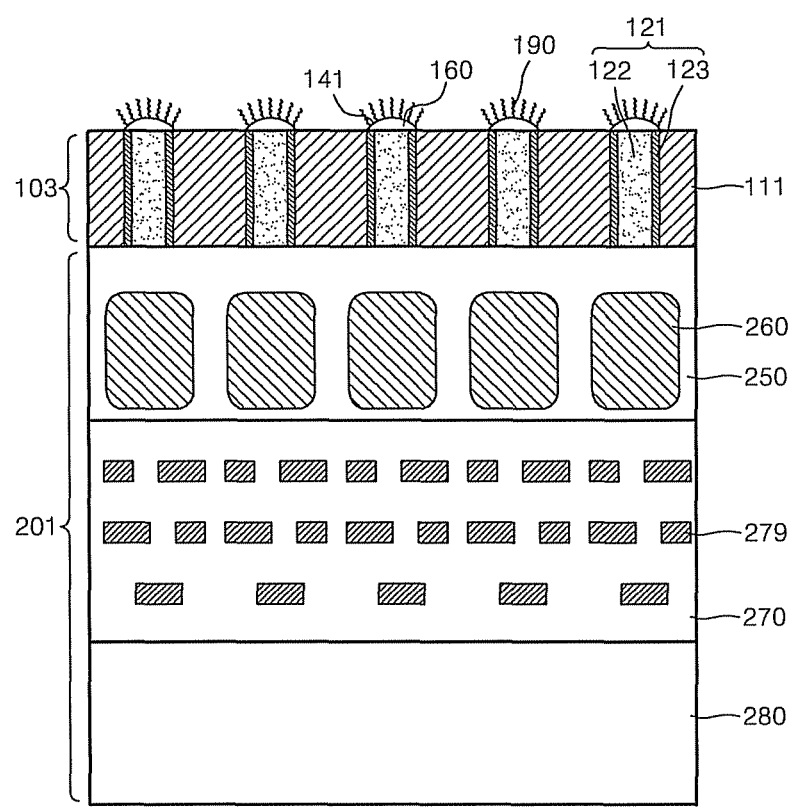
FIG. 7 is a schematic cross-sectional view of another embodiment of an integrated bio-chip according to the present disclosure.

FIG. 7 is a schematic cross-sectional view of another embodiment of an integrated bio-chip according to the present disclosure. Referring to FIG. 7, the integrated bio-chip includes the sample reaction portion 141, a sample detection portion 201, and the light transfer portion 103 located between the sample reaction portion 141 and the sample detection portion 201. The integrated bio-chip of the present embodiment is substantially similar to the embodiment of an integrated bio-chip described with reference to FIG. 3 except for that in the present embodiment the light transfer portion 103 further includes the micro lenses 160.

The light transfer portion 103 includes the substrate 111, a plurality of excitation light absorbing waveguides 121 penetrating through the substrate 111, and a plurality of micro lenses 160 disposed on upper portions of the plurality of excitation light absorbing waveguides 121. Each of the excitation light absorbing waveguides 121 includes the color filter core 122 and the clad layer 123.

The micro lenses 160 correspond to the end portions of the excitation light absorbing waveguides 120 in a one-to-one correspondence. A surface of the micro lens 160 becomes a reaction region to which samples are attached, and a peripheral portion of the micro lens 160 becomes a non-reaction region to which the samples are not attached. The micro lens 160 of the present embodiment is substantially similar to the micro lens described with reference to FIG. 5.

The sample detection portion 201 of the present embodiment includes the photodiode portion 250 including a plurality of photodiodes 260, the distribution line portion 260 including the control circuit for processing signals and the distribution lines 279, and a dummy substrate 280 supporting the photodiode portion 250 and the distribution line portion 270 thereon. In addition, the sample detection portion 201 is a back illumination type image sensor, in which the photodiode portion 250 is adjacent to the light transfer portion 101. The sample detection portion 201 of the present embodiment is substantially similar to the sample detection portion described with reference to FIG. 4.

Figure 8:
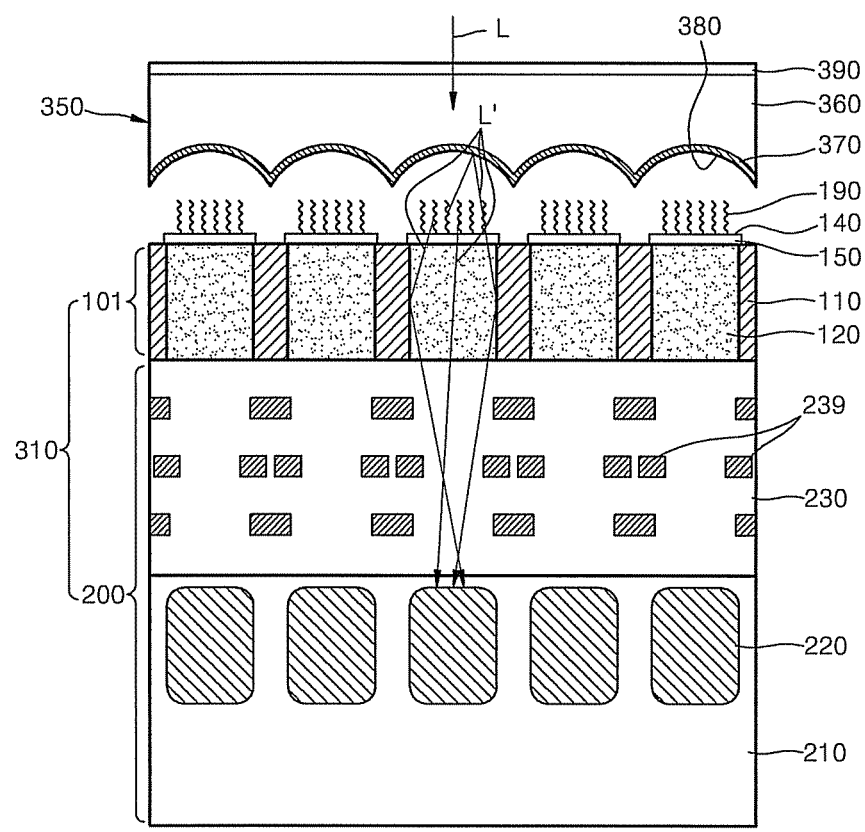
FIG. 8 is a schematic cross-sectional view of another embodiment of an integrated bio-chip according to the present disclosure.

FIG. 8 is a schematic cross-sectional view of another embodiment of an integrated bio-chip according to the present disclosure.

Referring to FIG. 8, the integrated bio-chip of the present embodiment includes an integrated chip 310 and a cover glass 350. The integrated chip 310 may be any one of the embodiments of integrated bio-chips according to the previous embodiments. For example, in one embodiment the integrated chip 310 includes the integrated bio-chip shown in FIG. 1, which includes the sample reaction portion 140, to which the samples are attached, the sample detection portion 200 for detecting the fluorescent light emitted from the samples, and the light transfer portion 101 located between the sample reaction portion 140 and the sample detection portion 200.

The cover glass 350 is a capping member for protecting the sample reaction portion 140 on which the target samples are attached, and is separated a predetermined distance from the sample reaction portion 140. The cover glass 350 includes a transparent body 360 and a fluorescent reflection layer 370 disposed under the transparent body 360. In one embodiment, the transparent body 360 is formed of a material that is transparent with respect to the excitation light.

The fluorescence reflection layer 370 transmits the excitation light and reflects the fluorescent light, and may be coated on a lower surface of the transparent body 370. In general, the wavelength of the fluorescent light is longer than that wavelength of the excitation light that excites the fluorescent light, and thus the light of the fluorescent wavelength may be reflected and the light of excitation light wavelength may be transmitted therethrough when the fluorescence reflection layer 370 is designed appropriately. A dichroic mirror that reflects the fluorescent wavelength or a band stop filter blocking the fluorescent wavelength may be adopted as the fluorescence reflection layer 370. In one embodiment, the band stop filter may be a notch filter that reflects the fluorescent wavelength.

The fluorescence reflection layer 370 reflects the fluorescent light proceeding upward from the samples 190 on the sample reaction portion 140. The fluorescence reflection layer 370 then reflects the fluorescent light downward to be detected by the sample detection portion 200, and thus, the sample detection efficiency may be improved greatly. In addition, since the band stopping property of the fluorescence reflection layer 370 is bi-directional, when white light is used as the excitation light, the fluorescent wavelength band included in the white light is removed by the fluorescence reflection layer 370 to reduce noise.

At least one micro mirror 380 may be formed on the lower surface of the transparent body 360. As shown in FIG. 8, the micro mirror 380 may be formed as a plurality of concave hemispheres in the lower surface of the transparent body 360. The micro mirror 380 has a concave curve, which has a property of condensing the reflected fluorescent light into the excitation light absorbing waveguide 120 and onto the photodiodes 220. The micro mirror 380 may correspond to the reaction regions 140a of the sample reaction portion 140 in one-to-one or one-to-many correspondence. In one embodiment, the fluorescent light proceeding upward may be effectively condensed in the reaction regions 140a of the sample reaction portion 140 by the micro mirror 380. The shape of the micro mirror 380 is not limited to the concave hemisphere shape shown in FIG. 8. Embodiments include configurations wherein the shape of the micro mirror 380 may vary depending on a shape of the reaction region 140a of the sample reaction portion 140 that will be described later, and may, for example, be a circle or a polygon. The curve of the micro mirror 380 may vary depending on a distance between the lower surface of the cover glass 350 and the reaction region 140a of the sample reaction portion 140.

As described above, since the fluorescent light L' emitted due to the excitation light L is non-directional, the fluorescent light L' radiates in all directions. Therefore, a large amount of the fluorescent light L' emitted due to the excitation light L proceeds upward. The fluorescent light L' proceeding upward is reflected by the fluorescence reflection layer 370 and is redirected toward the light transfer portion 100. As described above, when the condensing property of the micro mirror 380 is designed appropriately, the fluorescent light L' may be condensed in the incident end of the excitation light absorbing waveguide 120. Therefore, the fluorescent light L' proceeding upward may be used in the detection of a reaction at the samples 190, and the loss of the fluorescent light L' may be reduced. The cover glass 350 is disposed adjacent to the samples 190 within a range in which the cover glass 350 does not damage the samples 190, and thus, the cover glass 350 covers the samples 190 in the reaction regions 140*a* corresponding to the micro mirror 380 in order to improve light utilizing efficiency. Moreover, the fluorescent light L' emitted upward is condensed in the reaction region 140*a*, from which the fluorescent light itself is emitted, and thus, the blurring of fluorescent image due to the fluorescent light L' emitted from the neighboring samples 190 may be prevented.

In one embodiment, an anti-excitation light reflection layer 390 may be formed on an upper surface of the cover glass 350. The anti-excitation light reflection layer 390 has a anti-reflecting property of preventing a reflection of the excitation light L and transmitting the excitation light L. In addition, the anti-excitation light reflection layer 390 may be formed to have a shielding property with respect to the fluorescent wavelength.

In the embodiment of FIG. 8, the micro-mirror 380, the excitation light absorbing waveguide 120, and the photodiode 220 correspond to each other in one-to-one correspondence, however, alternative embodiments of the present disclosure are not limited thereto. For example, a plurality of micro mirrors 380 may correspond to one reaction region 140*a* of the sample reaction portion 140, or a plurality of reaction regions 140*a* to become one pixel unit. In addition, the photodiode 220 may be arranged to correspond to the exit end of the excitation light absorbing waveguide 120, which emits the fluorescent light, in one-to-one or one-to-many correspondence.

Figure 9:
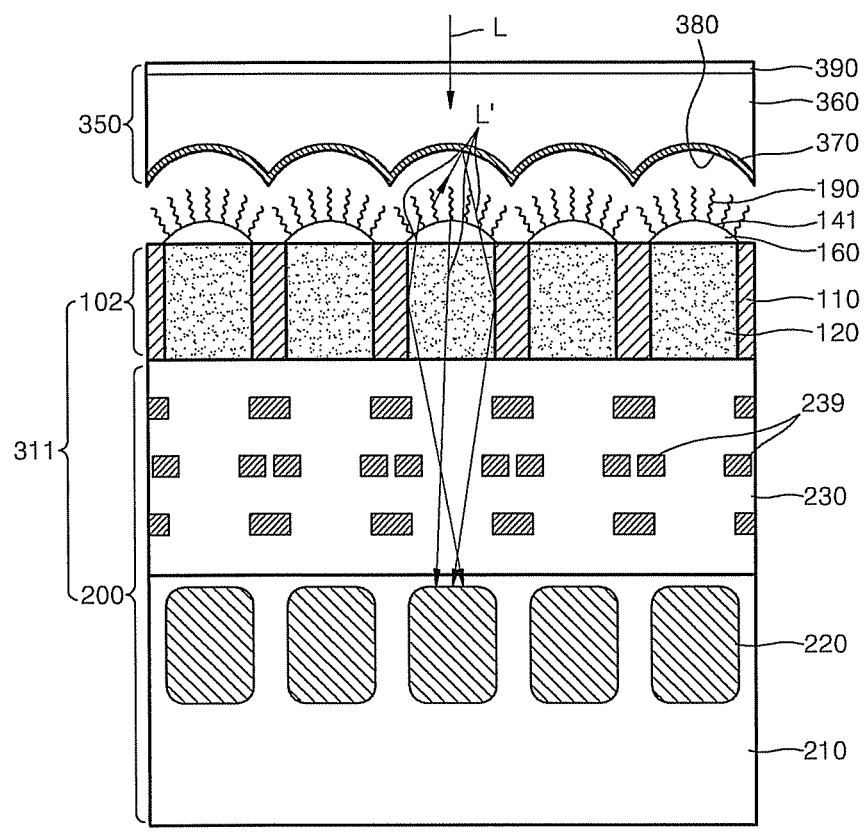
FIG. 9 is a schematic cross-sectional view of another embodiment of an integrated bio-chip according to the present disclosure.

FIG. 9 shows another embodiment of an integrated bio-chip according to the present disclosure. The integrated bio-chip of the present embodiment includes an integrated chip 311 and the cover glass 350. The integrated bio-chip of the present embodiment is substantially similar to the embodiment of an integrated bio-chip described with reference to FIG. 8 except for that the light transfer portion 102 further includes the micro lens 160. The integrated chip may be one of the previously described embodiments of integrated bio-chips, for example, it may be the embodiment of an integrated bio-chip shown in FIG. 5, which includes the sample reaction portion 141 to which the samples may be attached, the sample detection portion 200 for detecting the fluorescent light emitted from the samples, and the light transfer portion 102 located between the sample reaction portion 141 and the sample detection portion 200. The micro lens 160 is disposed on the incident end of the excitation light absorbing waveguide 120 of the light transfer portion 102. The micro lens 160 increases an efficiency of coupling the light L incident in the micro lens 160 to the excitation light absorbing waveguide 120, and condenses the light in the sample detection portion 200 to increase the fluorescent light detecting efficiency.

The cover glass 350 is a capping member for protecting the sample reaction portion 140, on which the target samples are attached, and is substantially similar to the cover glass 380 described with reference to the embodiment illustrated in FIG. 8.

Figure 10:
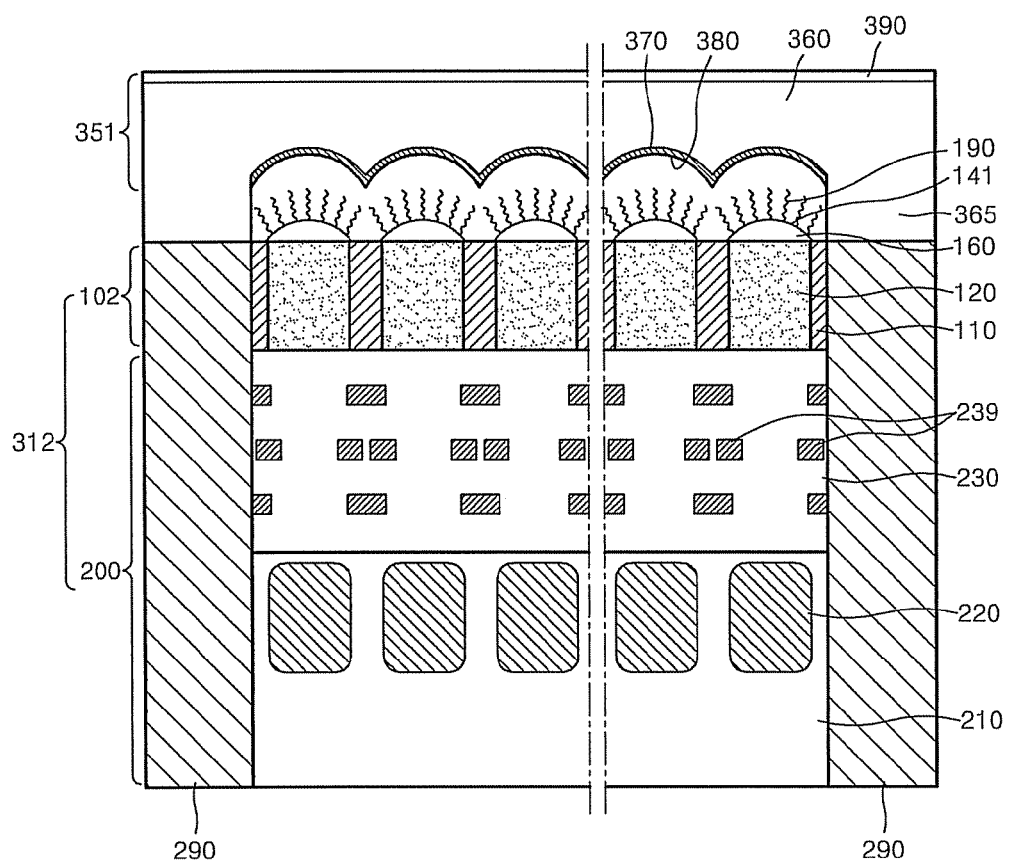
FIG. 10 is a schematic cross-sectional view of another embodiment of an integrated bio-chip according to the present disclosure.

FIG. 10 shows another embodiment of an integrated bio-chip according to the present disclosure. In the present embodiment, a cover glass 351 is physically coupled to the integrated chip 312.

In one embodiment, the integrated chip 312 may be fabricated in a wafer unit through semiconductor processes that will be described later. In such an embodiment an outer portion 290 of the integrated chip 312 is a space for processing signals of the sample detection portion 200 or from an electrical connection, e.g., a distribution line portion 230. The outer portion 290 of the integrated chip 312 may be coupled to the cover glass 351.

The transparent body 360 of the cover glass 351 has a side wall 365 that protrudes downward around the transparent body 360, and thus, contacts an upper surface of the outer portion 290 of the integrated chip 312. In one embodiment, the side wall 365 may be formed only on a part of the outer circumference of the transparent body 360. The cover glass 351 has an inner space due to the side wall 365 so that the samples 190 attached to the sample reaction portion 141 of the integrated chip 312 may not be damaged. Embodiments include configurations wherein alignment marks (not shown) are disposed on a wafer on which the integrated chip 312 is formed and/or the cover glass 351 so that the micro mirror 380 of the cover glass 351 and the reaction region of the sample reaction portion 141 may be aligned accurately when the cover glass 351 and integrated chip 312 are coupled to each other.

Figure 11:
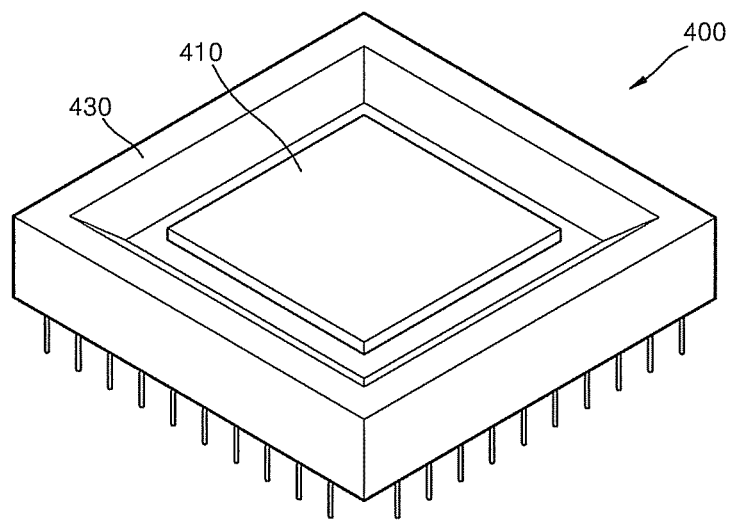
FIG. 11 is a schematic perspective view of another embodiment of an integrated bio-chip according to the present disclosure.

FIG. 11 shows another embodiment of an integrated bio-chip 400 according to the present disclosure. Referring to FIG. 11, the integrated bio-chip 400 of the present embodiment is packaged, and an integrated chip 410 is mounted on a frame 430. In the present embodiment, the integrated chip 410 is a chip including the sample reaction portion (140 of FIG. 1 or 141 of FIG. 5), the light transfer portion (100 of FIG. 1, 101 of FIG. 2, 102 of FIG. 5, or 103 of FIG. 6), and the sample detection portion (200 of FIG. 1 or 201 of FIG. 3). An upper surface of the integrated chip 410 is a surface, on which the sample reaction portion 140 or 141 is disposed, and may be exposed to an outside. In an embodiment wherein the bio-chip 400 is a DNA chip, probe nucleotides of a plurality of kinds are attached to the sample reaction portion 140 or 141 of the integrated chip 410 through the semiconductor processes. When a liquid including the target nucleotides flows on the surface of the DNA chip, the probe nucleotides having sequences complementary to those of the target nucleotides are combined with the target nucleotides via a hybridization reaction, and the nucleotides that are not combined with the probe nucleotides of the DNA chip are washed off. When exposed to an excitation light, the nucleotide that is hydrodized emits the fluorescent light due to the fluorescent material tagged thereon, and thus, it may be determined whether the target nucleotide exists within the sample or not by detecting the location from which the fluorescent light is emitted.

Figure 12:
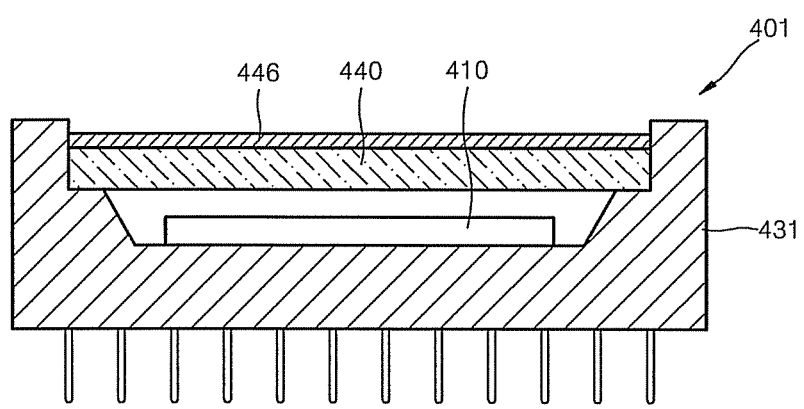
FIG. 12 is a schematic cross-sectional view of another embodiment of an integrated bio-chip according to the present disclosure.

FIG. 12 is a cross-sectional view of another embodiment of an integrated bio-chip 401 according to the present disclosure. Referring to FIG. 12, the integrated bio-chip 401 of the present embodiment is packaged, and includes the integrated chip 410, a frame 431, on which the integrated chip 410 is mounted and a cover glass 440 protecting the integrated chip 410. The integrated bio-chip 401 of the present embodiment is substantially similar to the embodiment of an integrated bio-chip 400 shown in FIG. 11 except for that the cover glass 440 is further formed thereon.

The cover glass 440 may be detachably installed, or a path (not shown) for inducing/discharging fluid including samples may be formed in a side of the cover glass 440. An anti-excitation light reflection layer 446 that prevents the excitation light for detecting samples from being reflected may be coated on an outer surface of the cover glass 440. The cover glass 440 prevents a surface of the integrated chip 410 from being damaged when the integrated bio-chip 401 is used.

Figure 13:
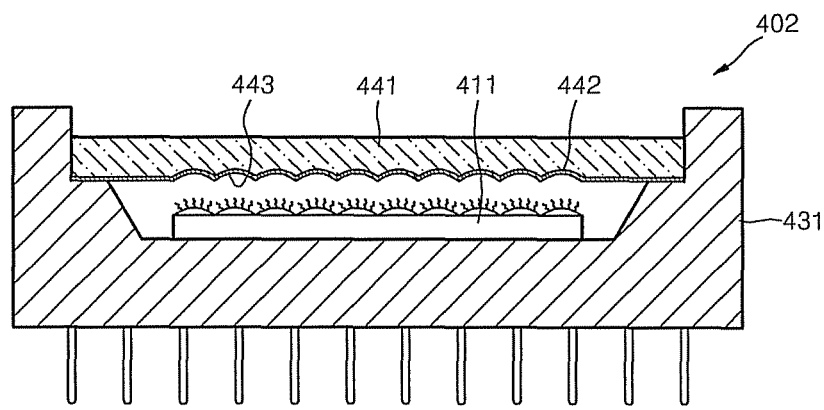
FIG. 13 is a schematic cross-sectional view of another embodiment of an integrated bio-chip according to the present disclosure.

FIG. 13 is a cross-sectional view of another embodiment of an integrated bio-chip 402 according to the present disclosure. Referring to FIG. 13, the integrated bio-chip 402 of the present embodiment is packaged, and includes an integrated chip 411, a frame 431, on which the integrated chip 411 is mounted, and a cover glass 441 protecting the integrated chip 411. The integrated bio-chip 402 of the present embodiment is substantially similar to the embodiment of an integrated bio-chip 401 described with reference to FIG. 12 except for the cover glass 441 includes a fluorescent reflection layer 442 and a micro lens 443. According to the integrated bio-chip 402 of the present embodiment, the fluorescent light proceeding upward from the samples is also used to detect the samples due to reflection by the fluorescence reflection layer 442 formed in the cover glass 441, and thus, the light utilizing efficiency is improved. In addition, the fluorescent light proceeding upward is condensed again in the emitted portion by to the micro lens 443, and thus, the blurring of fluorescent image due to the fluorescent light emitted from the neighboring samples may be prevented.

Next, an embodiment of processes of fabricating an integrated bio-chip according to the present disclosure will be described with reference to FIGS. 14A through 14F.

Figure 14A:
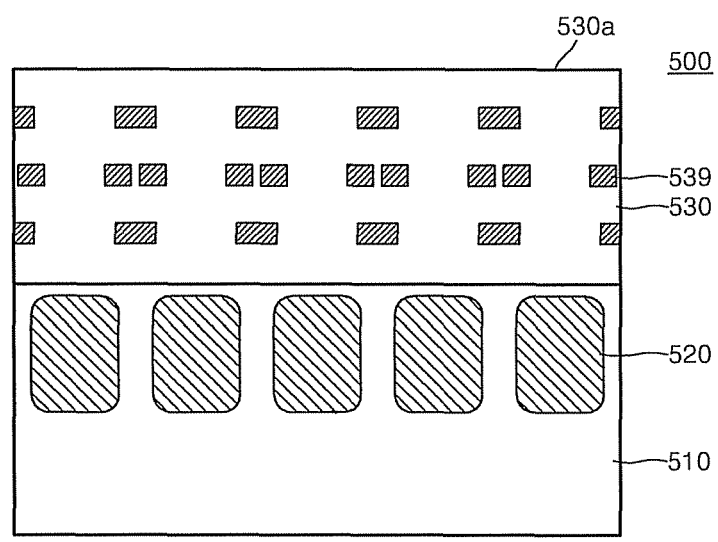
FIGS. 14A through 14F are cross-sectional views illustrating an embodiment of a method of fabricating an embodiment of an integrated bio-chip according to the present disclosure.

Referring to FIG. 14A, a sample detection portion 500 is prepared. The sample detection portion 500 of the present embodiment may be any one of a group of well known image sensors, and may be fabricated through well known processes. For example, in one embodiment a substrate on which a CMOS image sensor is disposed may be used as the sample detection portion 500. In such an embodiment, photodiodes 520 are stacked on a silicon substrate using a front end process to form the photodiode portion 510, and a distribution line portion 530 including CMOS circuitry and distribution lines 539 is formed on the photodiode portion 510. In addition, vertical and horizontal passive metal layers that connect circuits formed in the photodiode portion 510 and the distribution line portion 530 are formed in a backend process, and then, a CMOS image sensor is fabricated. A process of forming a color filter in the CMOS image sensor may be further performed during a general processes of fabricating a CMOS image sensor, however, the processes of forming the sample detection portion 200 of the present embodiment does not include the above process of forming the color filter. As another example, in one embodiment a well known CCD image sensor or a well known PMT may be used as the sample detection portion 500.

Figure 14B:
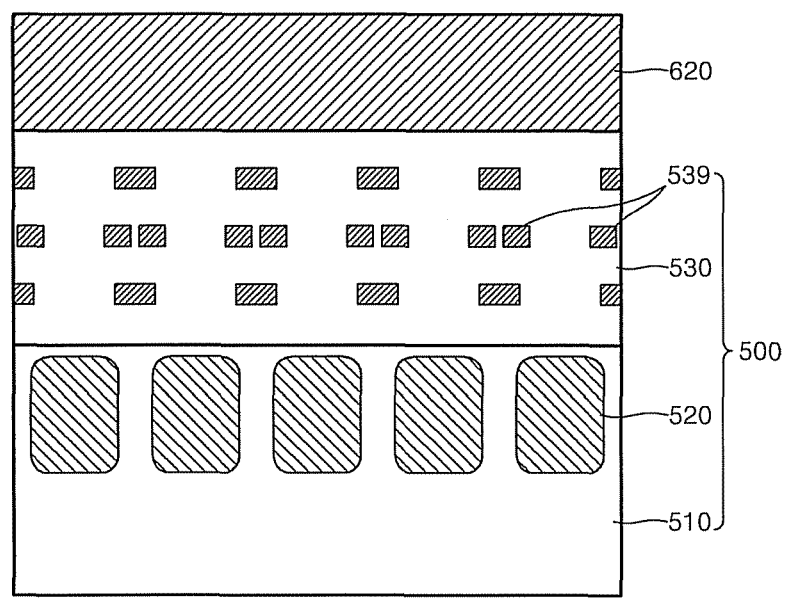
Figure 14C:
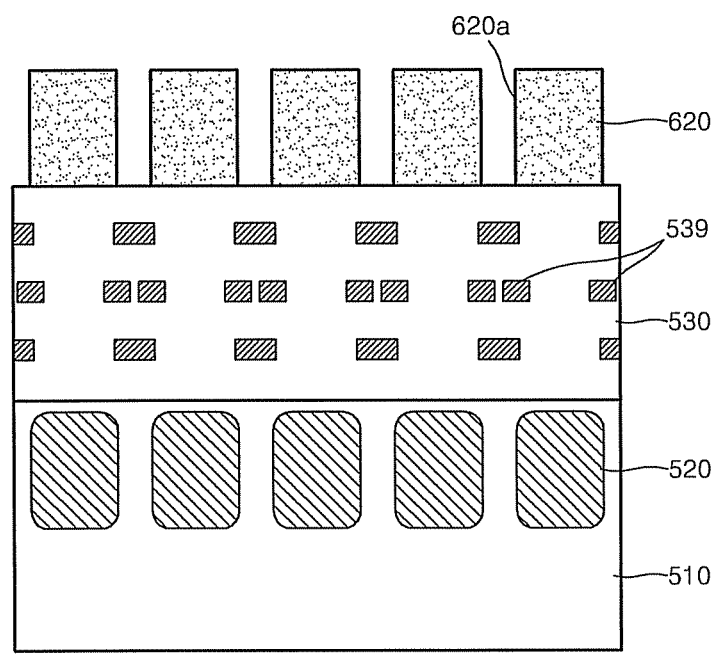
Figure 14D:
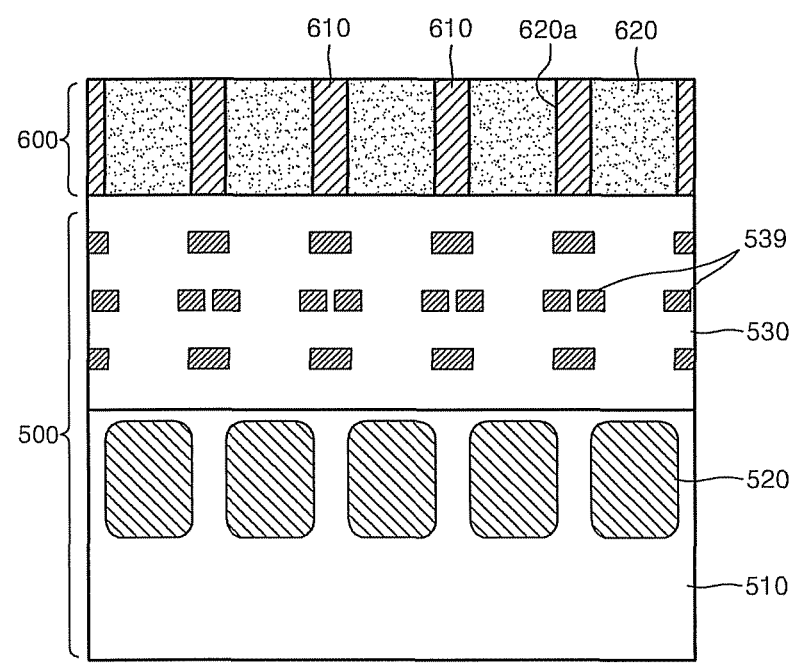

Next, as shown in FIGS. 14B through 14D, a light transfer portion 600 is formed on the sample detection portion 500.

Referring to FIG. 14B, an excitation light absorbing material is deposited on the sample detection portion 500, e.g., in a sputtering method, a chemical vapor deposition ("CVD") method, a spin-coating method or other similar method to form an excitation light absorbing material layer 620. The excitation light absorbing material is a material that absorbs light having the same or similar wavelength as the excitation light and transmits the light of the wavelength of the fluorescent light. For example, in one embodiment a transparent semiconductor material, polymer, dielectric material or other material having similar characteristics may be dyed using a dye having a wavelength similar to that of the fluorescent light, or the dye having the wavelength of the fluorescent light may be mixed with or dispersed in the transparent semiconductor material, the polymer, or the dielectric material. Since the pigment or dye is well known in the fields of displays or optics, additional detailed descriptions are not provided here.

Referring to FIG. 14C, trenches 620a are formed in the excitation light absorbing material layer 620 to expose upper portions of the sample detection portion 500 except for the locations where the photodiodes 520 are located. In one embodiment, the trenches 620a may be formed by a dry etching method. The excitation light absorbing material layer 620 in which the trenches 620a are formed correspond to the excitation light absorbing waveguides (120 of FIG. 1) of the previous embodiment.

Next, referring to FIG. 14D, a black material is filled in the trenches 620a formed in the excitation light absorbing material layer 620 to form the light blocking portion 610. In the present embodiment, the black material absorbs both of the excitation light and the fluorescent light. The excitation light absorbing material layer 620 and the light blocking portion 610 together form a light transfer portion 600.

Figure 14E:
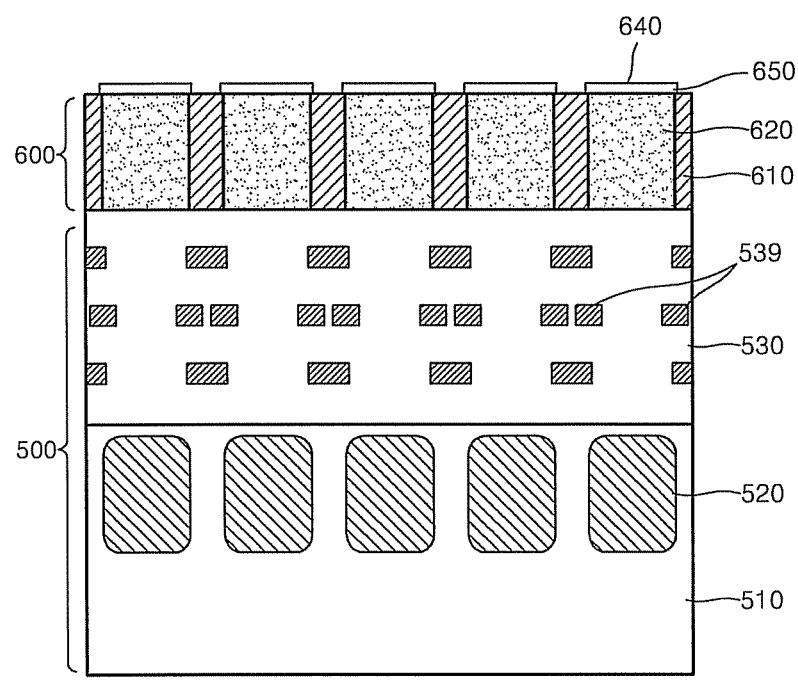

Next, referring to FIG. 14E, an upper surface of the light transfer portion 600 is planarized, e.g., by a process such as a chemical mechanical polishing ("CMP") process, and a fluorescence anti-reflection layer 650 is formed. The fluorescence anti-reflection layer 650 may be disposed on incident ends of the excitation light absorbing material layer 620. A surface of the fluorescence anti-reflection layer 650 is treated so that the samples may be attached well thereto, and becomes a sample reaction portion 640. In an alternative embodiment, instead of performing the surface treatment, the fluorescence anti-reflection layer 650 itself may be formed of a material that is affinitive to the samples.

Figure 14F:
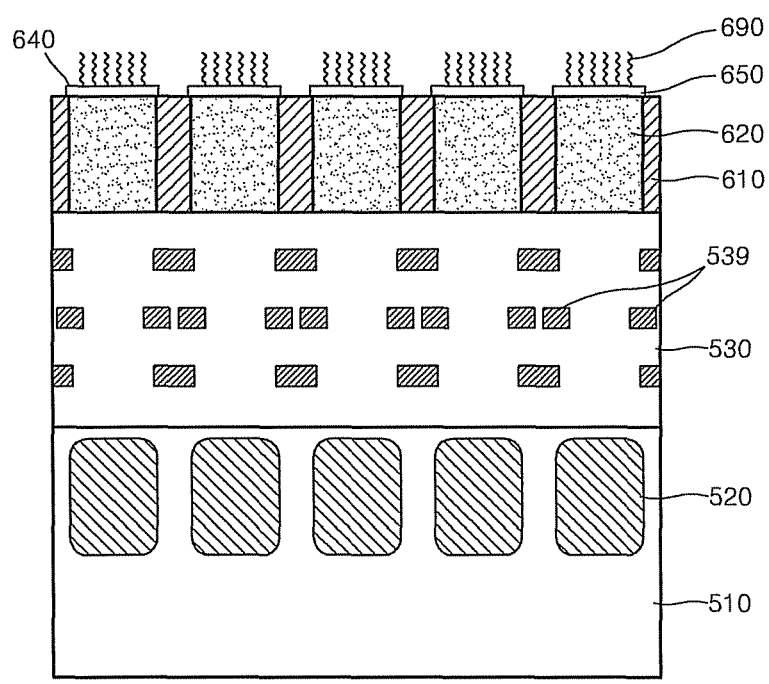

Next, referring to FIG. 14F, a process of attaching samples 690 to the sample reaction portion 640 is illustrated. The samples 690 may be probe bio-materials that interact with target bio-materials that are to be detected. For example, in one embodiment DNA bases such as adenine (A), guanine (G), cytosine (C), and thymine (T) are stacked on reaction regions in different sequences using a photolithography process, and thus, a DNA chip having probe DNAs having predetermined sequences may be fabricated.

In one embodiment, the above processes described with reference to FIGS. 14A through 14F may be performed in a wafer unit. That is, after fabricating the wafer, processes of dicing the wafer into chips and a wire bonding are performed to complete a bio-chip package.

Figure 15A:
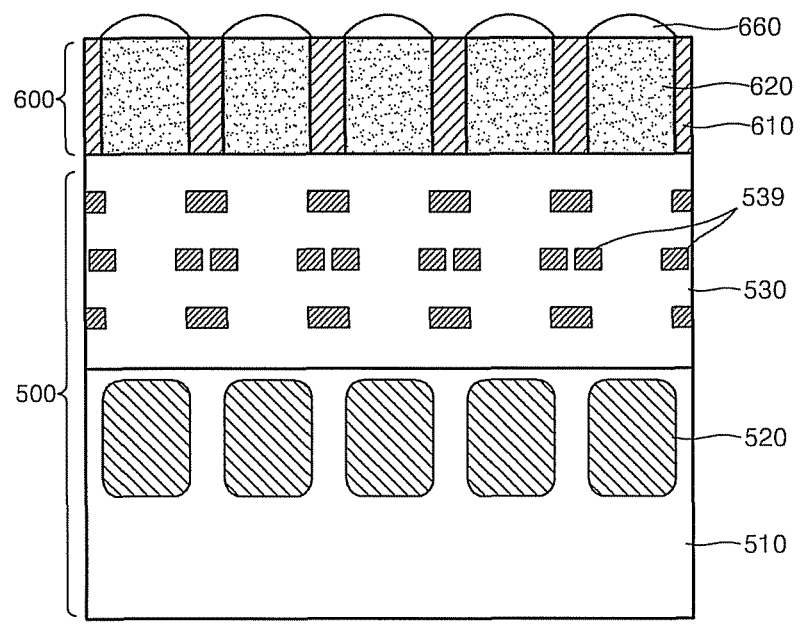
FIGS. 15A through 15B are cross-sectional views illustrating another embodiment of a method of fabricating an embodiment of an integrated bio-chip according to the present disclosure.
Figure 15B:
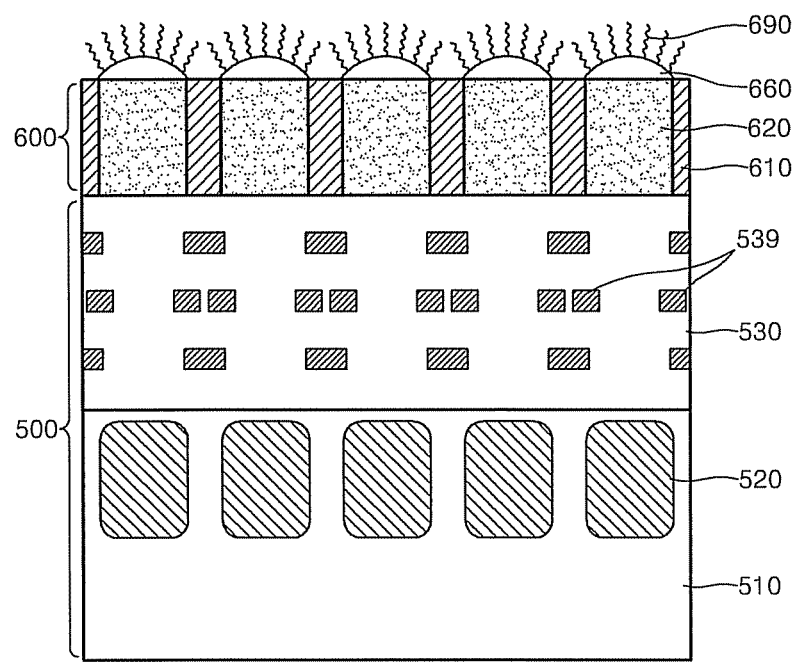

FIGS. 15A and 15B illustrate processes of fabricating another embodiment of an integrated bio-chip according to the present disclosure. The processes shown in FIGS. 15A and 15B further include a process of fabricating micro lenses 660 in addition to the processes described with reference to FIGS. 14A through 14F.

First, as shown in FIGS. 14A through 14D, the light transfer portion 600 including the light blocking portion 610 and the excitation light absorbing material layer 620 is formed on the sample detection portion 500, and the upper surface of the light transfer portion 600 is planarized by the CMP process.

Next, as shown in FIG. 15A, micro lenses 660 are formed on incident end regions of the excitation light absorbing material layer 620. The micro lenses 660 are formed by forming patterns of the micro lenses using photoresist, and reflowing the pillar-patterned photoresist into the photoresist having curves. A fluorescence anti-reflection layer (not shown) may be formed on surfaces of the micro lenses 660, and a surface of the fluorescence anti-reflection layer may be treated so that the samples are well attached thereto.

Referring to FIG. 15B, a process of attaching the samples 190 to the micro lenses 660 is performed. The samples 190 may be probe bio-materials that may interact with target bio-materials that are to be detected.

Figure 16A:
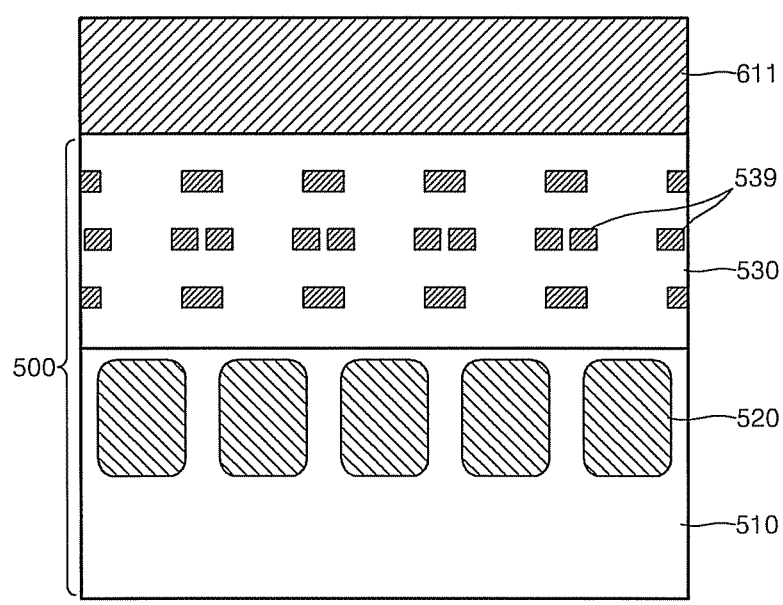
FIGS. 16A through 16C are cross-sectional views illustrating another embodiment of a method of fabricating an embodiment of an integrated bio-chip according to the present disclosure.
Figure 16B:
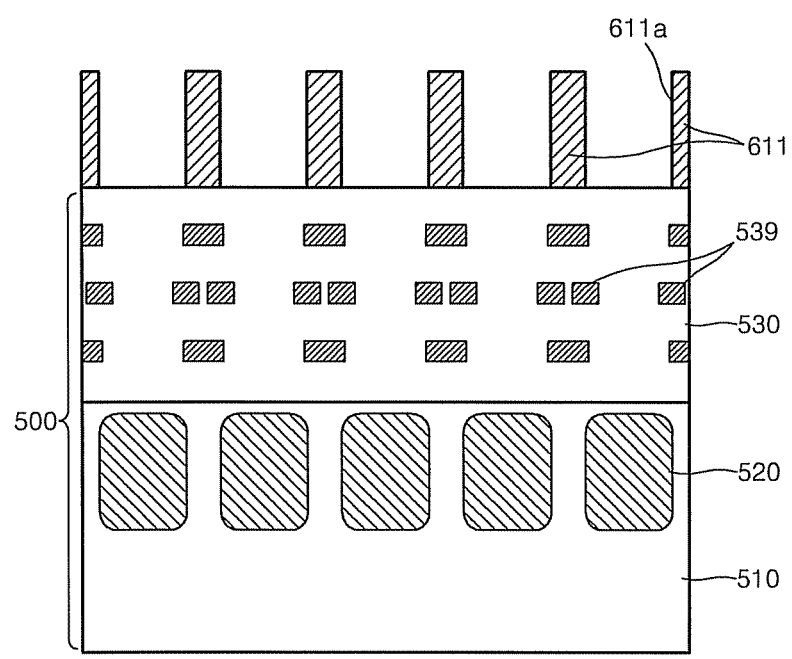
Figure 16C:
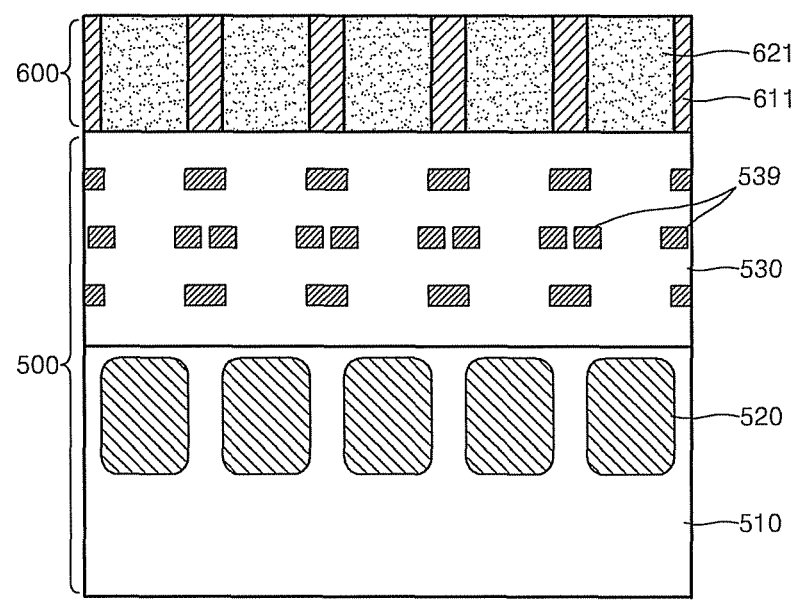

FIGS. 16A through 16C illustrate another embodiment of processes of fabricating an embodiment of an integrated bio-chip according to the present disclosure.

Referring to FIG. 16A, a black material is deposited on the sample detection portion 500 via a sputtering method, a CVD method, a spin-coating method or other similar method to form a black material layer 611. The black material absorbs both of the excitation light and the fluorescent light incident thereto.

Referring to FIG. 16B, trenches 611*a* are formed in the black material layer 611 to expose upper portions of the sample detection portion 500, which correspond to the locations of the photodiodes 520. In one embodiment, the trenches 611*a* may be formed by a dry etching method. The black material layer 611 in which the trenches 611*a* are formed correspond to the light transfer portion (110 of FIG. 1) of the previous embodiment.

Next, referring to FIG. 16C, an excitation light absorbing material having a refractive index that is lower than that of the black material is filled in the trenches 611*a* of the black material layer 611 to form excitation light absorbing waveguides 621. The excitation light absorbing material absorbs the light of the wavelength corresponding to the excitation light and transmits the light of wavelength corresponding to the fluorescent light. The excitation light absorbing material layer 621 and the light blocking portion 611 form the light transfer portion 601. In one embodiment, an upper surface of the light transfer portion 601 may be planarized by the CMP process.

As described with reference to FIGS. 14E and 14F, the fluorescence anti-reflection layer is formed on the upper surface of the light transfer portion 601 or the surface of the light transfer portion 601 is treated, and after that, the process of attaching samples is performed. In addition, as shown in FIGS. 15A and 15B, the process of forming the micro lenses 660 on the incident end portions of the excitation light absorbing material layer 621 may be further performed. In addition, the wafer may be diced into the chips, and the wire bonding process may be performed to finish the fabrication of the bio-chip package.

FIGS. 17A through 17H illustrate another embodiment of processes of fabricating an embodiment of an integrated bio-chip according to the present disclosure.

Figure 17A:
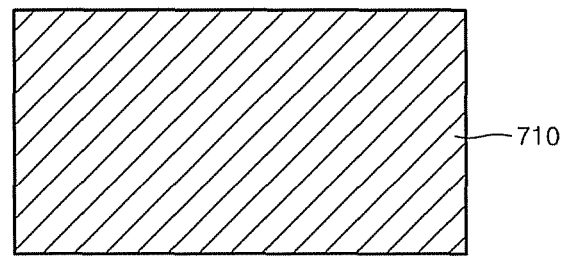
FIGS. 17A through 17H are cross-sectional views illustrating another embodiment of a method of fabricating an embodiment of an integrated bio-chip according to the present disclosure.

First, a substrate 710 is prepared as shown in FIG. 17A. Embodiments of the substrate 710 may be formed of a glass material, a semiconductor material, a metal material, a dielectric material, a polymer or various other similar materials. The substrate 710 may be formed of a material that is not affinitive to samples or liquid in which the samples are dispersed. For example, the substrate 710 may be a silicon substrate having a hydrophobic property. A surface of the substrate 710 may be formed as a planarized layer or may be planarized using a CMP process.

Figure 17B:
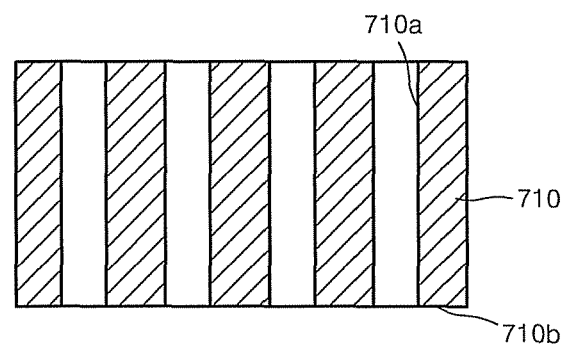

Next, referring to FIG. 17B, a plurality of penetration holes 710*a* are formed in the substrate 710. A diameter of each penetration hole 710*a* may range from a sub μm range to tens of μm. A through silicon via ("TSV") process, in which the penetration hole having a diameter of a few μm is formed in a silicon substrate having a thickness of a range of tens of μm, is well known in the art, and thus, in at least one embodiment, the penetration holes 710*a* may be formed using the TSV process.

When the diameter of the penetration hole 710*a* is very small, the penetration hole 710*a* may not penetrate through the substrate 710. In this case, a bottom surface 710*b* of the substrate 710 may be polished up to a point that is deeper than a length of the penetration hole 710*a* (such a process is also referred to as a back-lap process) so that the penetration hole 710*a* may penetrate the substrate 710. The back-lap process may be performed after forming excitation light absorbing waveguides that will be described later or after processing the surface of the substrate.

Figure 17C:
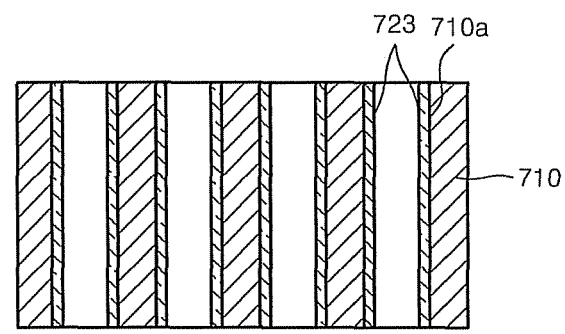

Referring to FIG. 17C, an inner wall surface of the penetration hole 710*a* in the substrate 710 is oxidized to lower a refractive index thereof, and then, a clad layer 723 is formed. The refractive index may be adjusted by controlling the oxidization level or by adding a dopant to the clad layer 723. The clad layer 723 may be formed by injecting the dopant in the penetration hole 710*a* to disperse the dopant on the inner wall surface of the penetration hole 710*a*, or by applying a material having a low refractive index on the inner wall surface of the penetration hole 710*a*.

Figure 17D:
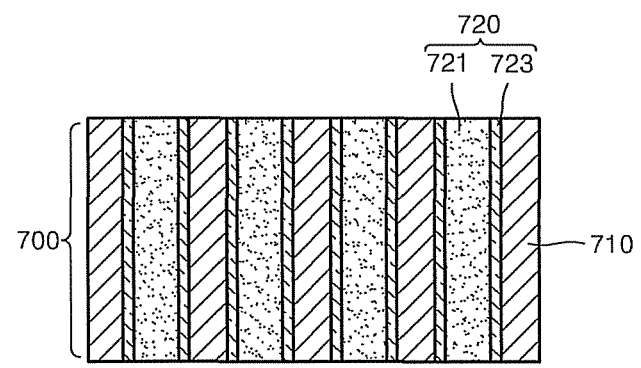

Referring to FIG. 17D, a color filter material is filled in the penetration hole 710*a* in which the clad layer 723 is formed, in order to form a color filter core 721. The color filter material is combined with a dye or a pigment having a fluorescent wavelength band using a transparent binder, and has a refractive index that is greater than that of the clad layer 723. The color filter core 721 and the clad layer 723 form an excitation light absorbing waveguide 720. As described above, the excitation light absorbing waveguide 720 is formed by penetrating through the substrate 710, and then, the light transfer portion 700 is formed. After filling the color filter material, the surface of the light transfer portion 700 may be planarized using the CMP process.

Figure 17E:
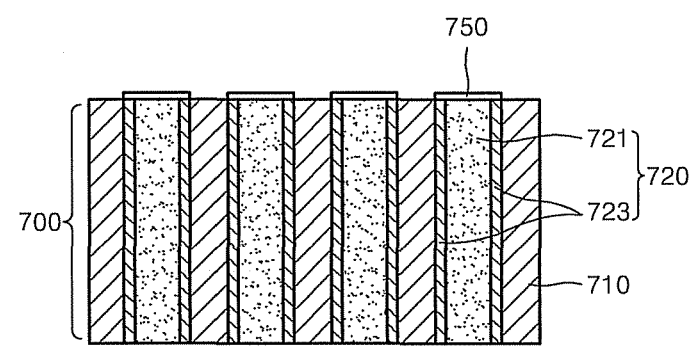

Referring to FIG. 17E, a fluorescence anti-reflection layer 750 is formed on an upper surface of the light transfer portion 700. The fluorescence anti-reflection layer 750 is formed on exposed portions of the clad layer 723 and the color filter core 721 on the substrate 710. In one embodiment, the fluorescence anti-reflection layer 750 may be formed using a photolithography process and a deposition process.

Figure 17F:
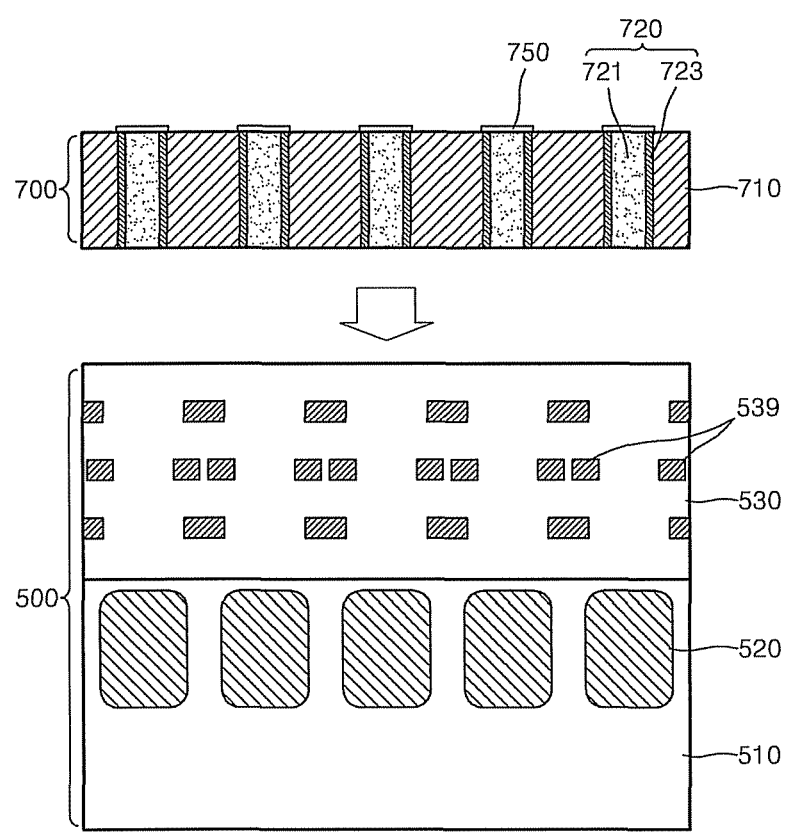

Next, as shown in FIG. 17F, the light transfer portion 700 is bonded to the sample detection portion 500. The sample detection portion 500 is substantially similar to the well known image sensor as shown in FIG. 14A, and may be fabricated through well known processes. The bonding of the light transfer portion 700 to the sample detection portion 500 may be performed in a wafer unit or a single chip unit. For example, in one embodiment the light transfer portion 700 and the sample detection portion 500 may be aligned with each other using alignment marks, and then, directly bonded to each other in the wafer unit. The direct bonding may be performed by applying a predetermined pressure to the aligned substrate to fuse the bonding surface, or using plasma. In one embodiment, a bonding pad may be attached to the bonding surface in advance, and then, the bonding process may be performed.

Figure 17G:
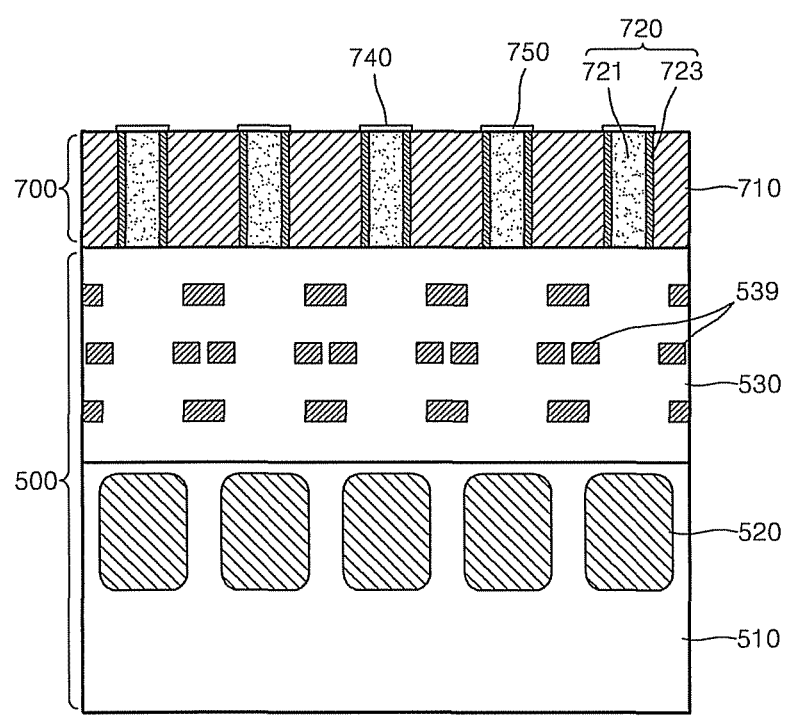

Referring to FIG. 17G, incident end portions of the excitation light absorbing waveguides 720 are treated so that the samples may be well attached thereto to form a sample reaction portion 740. The surface treatment may be performed before bonding the light transfer portion 700 and the sample detection portion 500. The sample reaction portion 740 may be the surface of the fluorescence anti-reflection layer 750. If the fluorescence anti-reflection layer 750 is affinitive to the samples, the surface treatment process may be substituted by the process of forming the fluorescence anti-reflection layer 750.

Figure 17H:
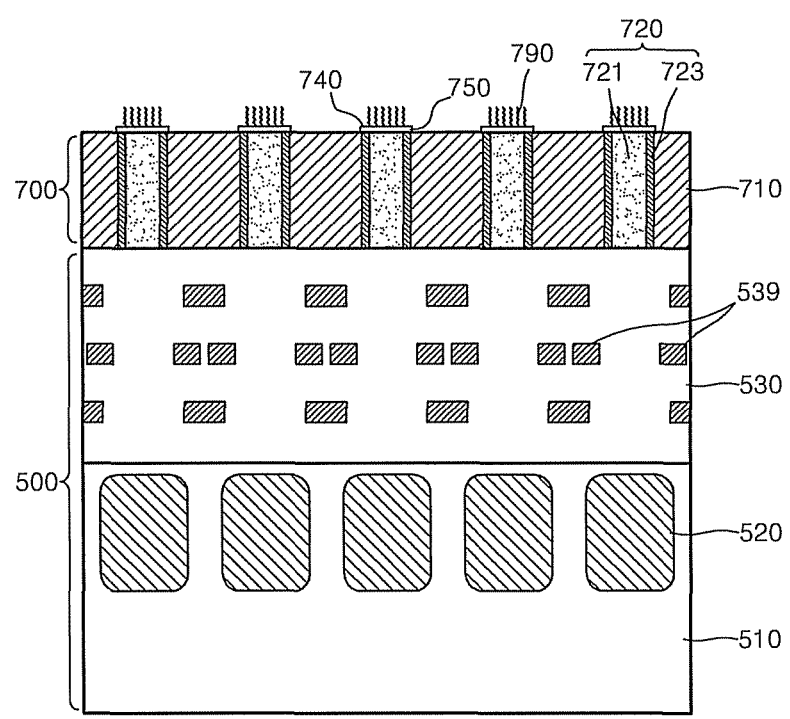

Next, referring to FIG. 17H, a process of attaching samples 790 to the sample reaction portion 740 on the upper portion of the light transfer portion 700 may be performed. The samples 790 may be probe bio-materials that may interact with the target bio-materials that are to be detected. In addition, at this point in the manufacturing process the wafer may be diced into chips, and a wire bonding process my be performed to complete the bio-chip packages.

Figure 18A:
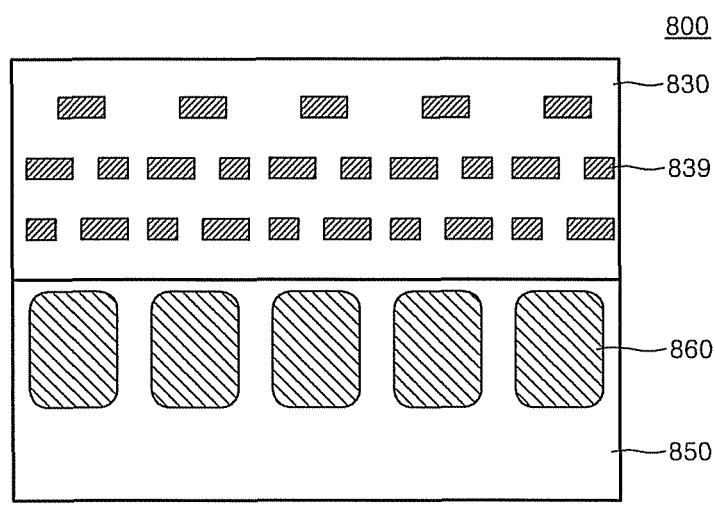
FIGS. 18A through 18F are cross-sectional views illustrating another embodiment of a method of fabricating an embodiment of an integrated bio-chip according to the present disclosure.
Figure 18B:
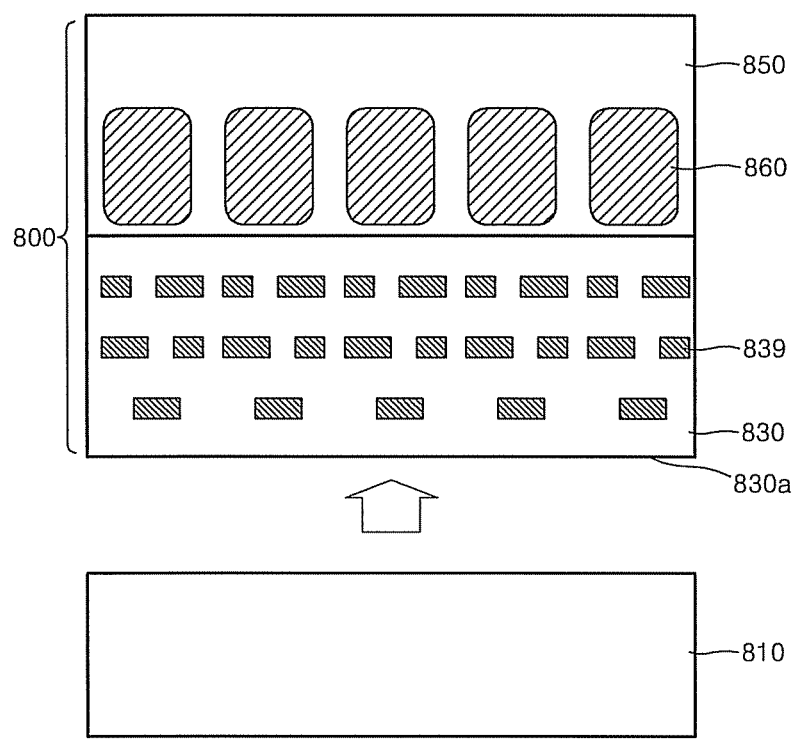
Figure 18C:
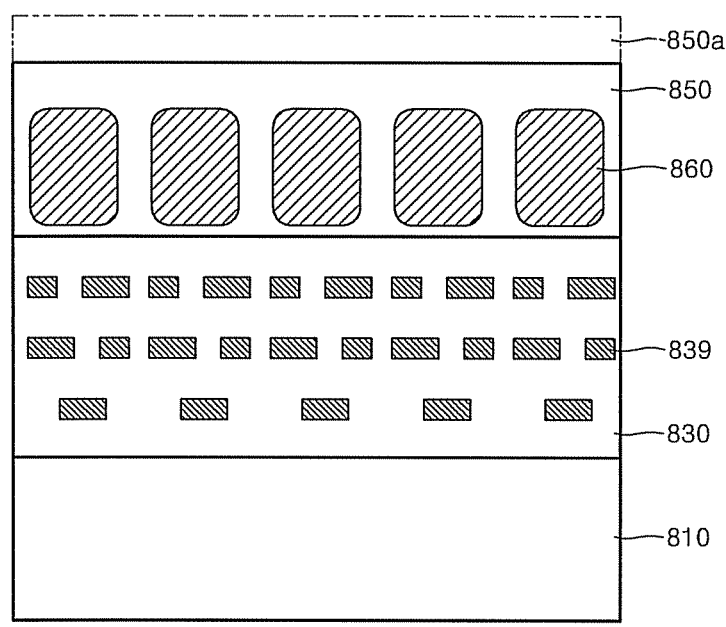

FIGS. 18A through 18C illustrate another embodiment of processes of fabricating an embodiment of an integrated bio-chip according to the present disclosure.

Referring to FIG. 18A, a sample detection portion 800 including a photodiode portion 850 and a distribution line portion 830 is prepared.

Next, referring to FIG. 18B, a dummy substrate 810 is bonded to the distribution line portion 830. The bonding between the distribution line portion 830 and the dummy substrate 810 may be performed using heat and pressure, and/or plasma. In one embodiment, a bonding pad may be attached to the bonding surface in advance, and then, the bonding process may be performed.

Referring to FIG. 18C, a grinding-thinning-polishing process of a rear surface of the photodiode portion 850 is performed to remove a part 850a of the photodiode portion 850 to reduce a thickness of the photodiode portion 850. The reduction in thickness may increase a detection accuracy of the resulting bio-material detecting apparatus.

Figure 18D:
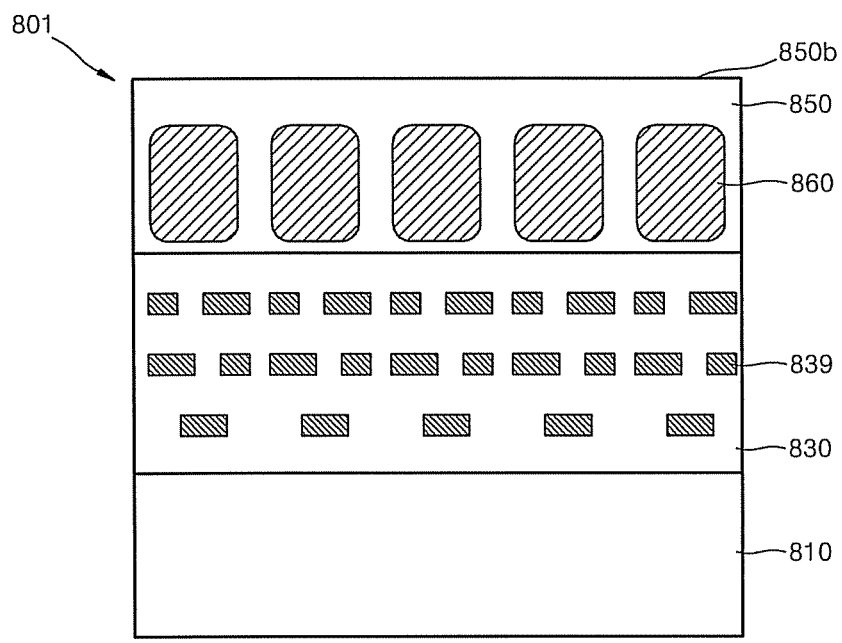

Next, referring to FIG. 18D, the surface 850b of the photodiode portion 850 is polished and treated so as to restrain generation of dark current or crosstalk, thereby resulting in a back illumination type sample detection portion 801. In one embodiment, the surface treatment method is, for example, a method of irradiating a laser beam to the surface 850b of the photodiode portion 850 to recrystallize it, or a passivation method using plasma.

The sample detection portion 801 of the present embodiment is substantially similar to a general back illumination type image sensor, and may be fabricated through the same fabrication processes. However, the process of fabricating the general back illumination type image sensor typically further include a process of providing a color filter, however, the processes of fabricating the sample detection portion 801 of the back illumination type of the present embodiment does not include the process of forming the color filter.

Figure 18E:
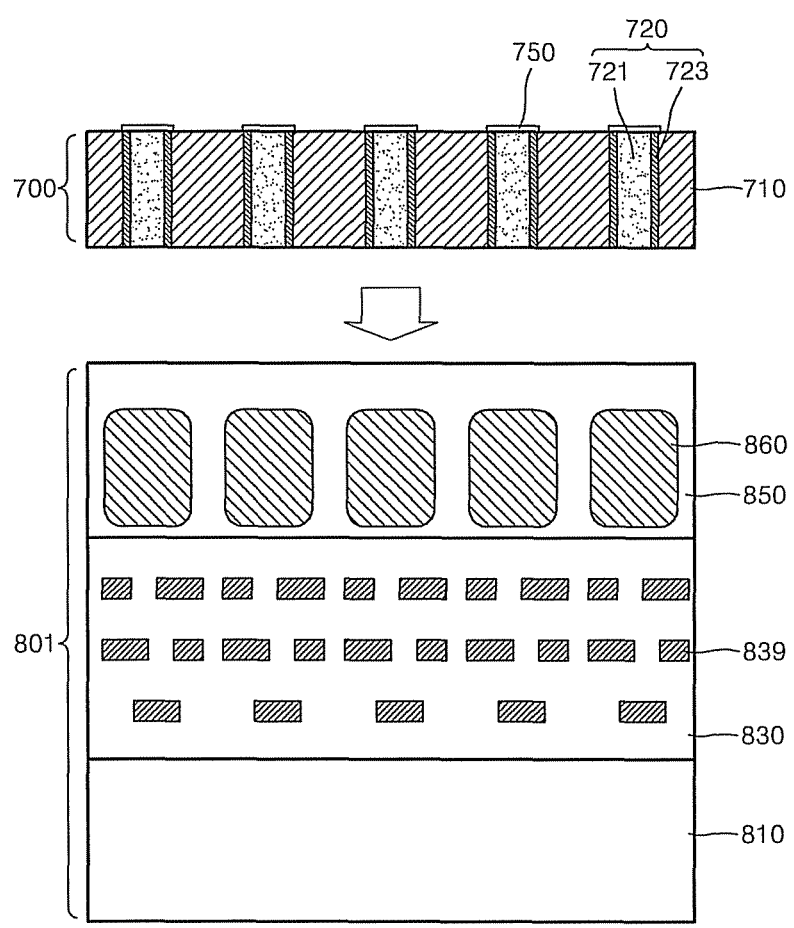

Next, as shown in FIG. 18E, the light transfer portion 700 and a surface of the sample detection portion 801 facing the photodiode portion 850 are bonded to each other. The light transfer portion 700 is substantially similar to the embodiment of a light transfer portion described with reference to FIGS. 17A through 17E. Embodiments of the bonding of the light transfer portion 700 and the sample detection portion 801 may be performed in the wafer unit or the single chip unit.

Figure 18F:
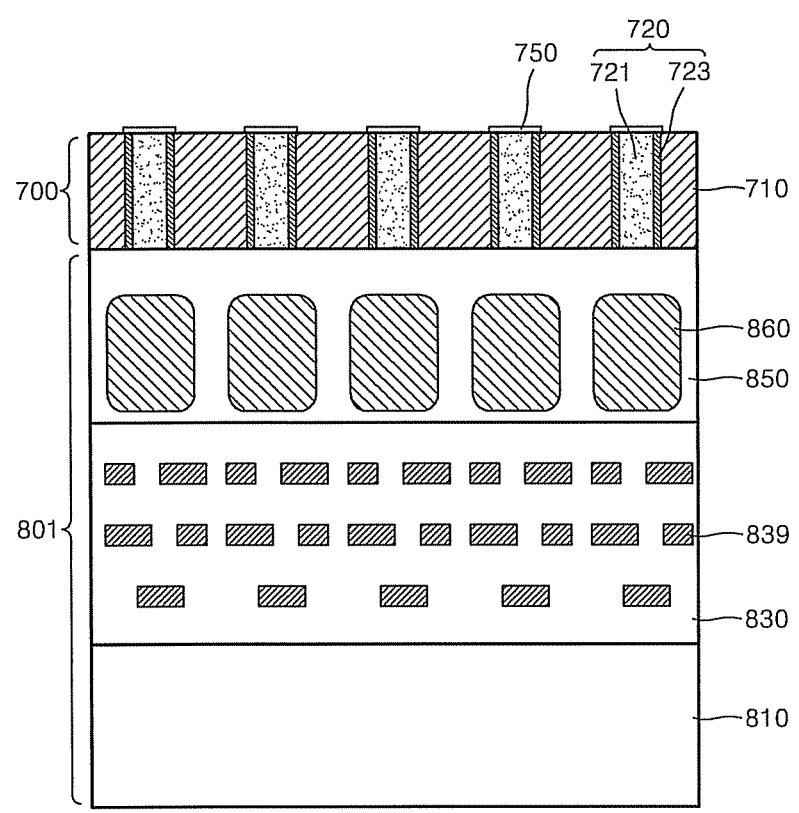

Next, referring to FIG. 18F, incident end portions of the excitation light absorbing waveguides 720 are treated so that the samples may be well attached to the light transfer portion 700. In one embodiment, the surface treatment may be performed before bonding the light transfer portion 700 and the sample detection portion 801. If the fluorescence anti-reflection layer 750 is affinitive to the samples, the surface treatment process may be substituted for the process of forming the fluorescence anti-reflection layer 750. Next, the samples are attached to the surface of the light transfer portion 700, the wafer may be diced into the chips, and the wire bonding process may be performed to complete the chip-chip packages.

Processes of fabricating an embodiment of a cover glass according to the present disclosure will be described with reference to FIGS. 19A through 19D.

Figure 19A:
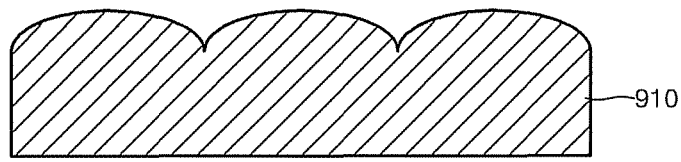
FIGS. 19A through 19D are cross-sectional views illustrating another embodiment of a method of fabricating an embodiment of an integrated bio-chip according to the present disclosure.
Figure 19B:
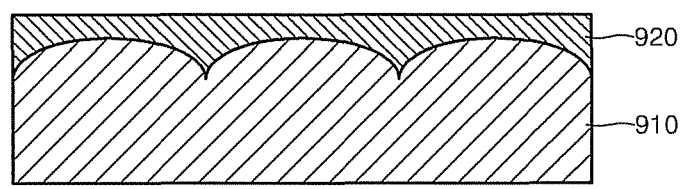
Figure 19C:
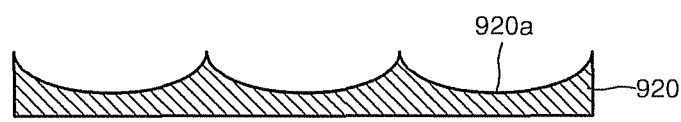
Figure 19D:
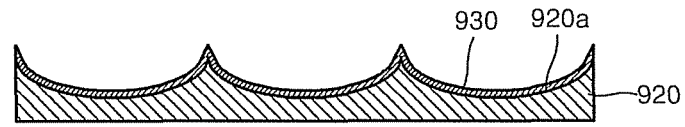

Referring to FIG. 19A, a convex micro lens mold 910 is prepared. For example, in one embodiment the micro lens mold 910 maybe formed by forming a photoresist having a pillar shape on a substrate through a photoresist process and an etching process, and subsequently changing the pillar-shaped photoresist to rounded photoresist through a reflow process. Referring to FIGS. 19B and 19C, a transparent body 920 of the cover glass is fabricated using the micro lens mold 910. In one embodiment, the transparent body 920 may be fabricated of a material that may be detached easily from the micro lens mold 910. Due to the fabrication process, the transparent body 920 has concave surfaces 920a that are an inverse of the micro lens mold 910.

Next, referring to FIG. 19B, a fluorescence reflection layer 930 is coated on the concave surfaces 920a of the transparent body 920 to form the micro lenses, and then, the cover glass is fabricated.

The above embodiments of processes of fabricating the cover glass are the processes of forming the transparent body 920 using a molding process. However, other various processes may be used to form the cover glass. For example, in one embodiment the concave surfaces formed as hemispheres may be directly formed in a transparent substrate to form the cover glass.

The cover glass covers the sample reaction portion of the bio-chip when the samples are attached on the bio-chip, and then, the bio-chip is completed. As described above, alignment marks may be formed in the cover glass and upper portion of the bio-chip, and thus, when the cover glass is coupled to the bio-chip, the cover glass and the bio-chip may be aligned precisely using an optical device at high magnification.

Hereinafter, an embodiment of a detection apparatus using the integrated bio-chip of the previous embodiments will be described as follows.

Figure 20:
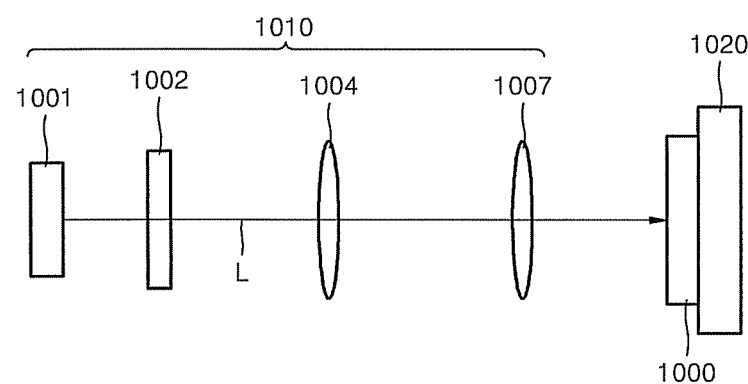
FIG. 20 is a schematic block diagram of an embodiment of a bio detecting apparatus according to the present disclosure.

FIG. 20 is a schematic block diagram of an embodiment of a bio-material detecting apparatus according to the present disclosure. The bio-material detecting apparatus of the present embodiment includes an illumination optics 1010 irradiating excitation light to an integrated bio-chip 1000, and a stage 1020 on which the bio-chip 1000 is detachably installed. The illumination optics 1010 includes a light source 1001, a light diffusing device 1002, a collimating lens 1004, and a condensing lens 1007. Alternative embodiments may include additional elements or fewer elements than that described with respect to the present embodiment.

The light source 1001 emits excitation light L. The excitation light L is for exciting fluorescent materials attached on the bio-materials in the integrated bio-chip 250. In general, a light having a wavelength of about 500 nm is used as the excitation light L, however, the wavelength of the excitation light L may be different according to the fluorescent materials tagged on the bio-materials. Embodiments of the light source 1001 may be any kind of device that may emit the excitation light L. For example, in one embodiment a semiconductor laser diode, a light emitting diode ("LED"), a white light source or various other similar light sources may be used as the light source 1001. When the white light source is used as the light source 1001, an excitation filter (not shown) that blocks the light having the wavelength band of the fluorescent light is disposed on an optical path between the light source 1001 and the integrated bio-chip 1000.

The light diffusing device 1002 diffuses the excitation light L evenly so that the excitation light L has an even intensity throughout the entire cross section thereof, for example, the light diffusing device 1002 may be a bar type light integrator. The excitation light L has uniform intensity throughout the entire cross section thereof so that light with constant intensity is irradiated to a selected region, or the entire surface, of the integrated bio-chip 1000.

The collimating lens 1004 changes the excitation light L into parallel light. In FIG. 20, the collimating lens 1004 is disposed between the light diffusing device 1002 and the condensing lens 1007, however, alternative embodiments include configurations wherein the collimating lens 1002 may be disposed between the light source 1001 and the light diffusing device 1002. Moreover, when the excitation light L emitted from the light source 1001 does not diverge much and the condensing lens 1007 may sufficiently condense the excitation light L, the collimating lens 1004 may be omitted.

The condensing lens 1007 condenses the excitation light L so that a light spot having a predetermined diameter is formed on the integrated bio-chip 1000. The diameter of the light spot may cover only a portion of the integrated bio-chip 1000 or the entire region of the integrated bio-chip 1000.

When the light spot of the excitation light L covers the entire surface of the integrated bio-chip 1000, the integrated bio-chip 1000 may detect simultaneously all of the fluorescent images emitted from the samples. When the light spot of the excitation light L covers only a part of the integrated bio-chip 1000, the stage 1020 or the illumination optics 1010 moves to sequentially cover the entire surface of the integrated bio-chip 1000 in a time-sequential manner. In addition, the integrated bio-chip 1000 may obtain the fluorescent images of the entire area of the integrated bio-chip by combining the fluorescent images emitted from the samples in a time-sequential order.

The integrated bio-chip 1000 of the present embodiment directly detects the fluorescent light emitted from the samples due to the irradiated excitation light L, and the signals of the detected fluorescent light are transferred to a signal processing system (not shown) through the stage 1020. in one embodiment, the stage 1020 itself may be a measuring board including a signal processing circuit.

According to the bio-material detecting apparatus of the present embodiment, the integrated bio-chip 1000 may directly read the fluorescent images emitted from the samples without including an additional detecting optics package. Therefore, the bio-material detecting apparatus may only include the illumination optics 1010, and thus, it is easy to fabricate a portable bio-material detecting apparatus. In addition, samples, such as the bio-materials, may be detected without regard to the locations where the bio-material detecting apparatus is installed.

According to the above embodiments, the sample reaction portion on which the bio-materials react, the light transfer portion transferring the fluorescent light emitted from the sample reaction portion, and the sample detection portion detecting the fluorescent light transferred from the light transfer portion are integrated as a chip, and thus, the integrated bio-chip and the bio-material detecting apparatus including the integrated bio-chip may be fabricated to be compact.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. An integrated bio-chip comprising:
    a sample detection portion including at least one light receiving device which detects fluorescent light emitted from at least one sample;
    a light transfer portion disposed on a light incident surface of the sample detection portion, and which includes at least one excitation light absorbing waveguide which absorbs an excitation light and transmits the fluorescent light emitted from the at least one sample;
    a sample reaction portion disposed adjacent to an incident end of the at least one excitation light absorbing waveguide, and including at least one reaction region on which the at least one sample is attached; and
    a micro lens disposed on a light incident end of the at least one excitation light absorbing waveguide,
    wherein the micro lens condenses the fluorescent light onto the light receiving device,
    wherein a surface of the micro lens provides the at least one reaction region, and
    wherein the sample detection portion, the light transfer portion, and the sample reaction portion are integrally coupled to each other as a single component.

2. The integrated bio-chip of claim 1, wherein the light transfer portion includes a light blocking portion which surrounds each of the at least one excitation light absorbing waveguide and which blocks the excitation light and the fluorescent light from traveling therethrough.

3. The integrated bio-chip of claim 2, wherein the light blocking portion includes a black material which absorbs the excitation light and the fluorescent light.

4. The integrated bio-chip of claim 2, wherein the at least one excitation light absorbing waveguide has a refractive index which is greater than a refractive index of the light blocking portion.

5. The integrated bio-chip of claim 1, wherein the excitation light absorbing waveguide includes a color filter core which transmits the fluorescent light emitted from the samples and absorbs the excitation light which excites the samples.

6. The integrated bio-chip of claim 5, wherein the color filter core has a refractive index which is greater than a refractive index of a substrate surrounding the color filter core.

7. The integrated bio-chip of claim 5, wherein the excitation light absorbing waveguide further comprises a clad layer disposed on a circumference of the color filter core and wherein the clad layer has a refractive index that is less than a refractive index of the color filter core.

8. The integrated bio-chip of claim 1, further comprising a fluorescence anti-reflection layer disposed on the at least one reaction region, wherein the fluorescence anti-reflection layer transmits the fluorescent light emitted from the at least one sample.

9. The integrated bio-chip of claim 1, wherein the sample detection portion is selected from the group consisting of a photo multiplier tube, a charge coupled device and a complementary metal oxide semiconductor image sensor.

10. The integrated bio-chip of claim 1, wherein the sample detection portion includes a front illumination type image sensor.

11. The integrated bio-chip of claim 1, wherein the sample detection portion includes a back illumination type image sensor.

12. The integrated bio-chip of claim 1, wherein the light receiving device of the sample detection portion corresponds to the at least one reaction region in one of a one-to-one correspondence and a one-to-many correspondence.

13. The integrated bio-chip of claim 1, further comprising a frame on which the sample reaction portion, the light transfer portion and the sample detection portion are disposed.

14. The integrated bio-chip of claim 1, further comprising a cover glass disposed spaced apart from the sample reaction portion, wherein the cover glass protects the sample reaction portion.

15. The integrated bio-chip of claim 14, wherein the cover glass includes a fluorescence reflection layer on an inner surface of the cover glass, wherein the fluorescence reflection layer reflects the fluorescent light emitted from the at least one sample.

16. The integrated bio-chip of claim 15, wherein the fluorescence reflection layer is one of a dichroic mirror which reflects a wavelength band corresponding to the fluorescent light and a band reject filter which shields a wavelength band corresponding to the fluorescent light.

17. The integrated bio-chip of claim 15, wherein the fluorescence reflection layer passes a wavelength band of the excitation light therethrough.

18. The integrated bio-chip of claim 14, wherein at least one micro mirror which condenses and reflects the fluorescent light emitted from the at least one sample is disposed on an inner surface of the cover glass.

19. The integrated bio-chip of claim 18, wherein the micro mirror is concave and reflects incident fluorescent light while condensing the fluorescent light emitted from the at least one sample.

20. The integrated bio-chip of claim 18, wherein the at least one micro mirror corresponds to the reaction region of the sample reaction portion in one of a one-to-one correspondence and a one-to-many correspondence.

21. The integrated bio-chip of claim 14, wherein an anti-excitation light reflection layer prevents the excitation light from being reflected on an outer surface of the cover glass.

22. A method of fabricating an integrated bio-chip of claim 1, the method comprising:
preparing a sample detection portion including at least one light receiving device;
providing a light transfer portion having at least one excitation light absorbing waveguide on a light incident surface of the sample detection portion; and
providing a sample reaction portion including at least one reaction region on which at least one sample is attached on an upper surface of the light transfer portion,
wherein the providing of the light tranfer portion further comprises disposing a micro lens on a light incident end of the at least one excitation light absorbing waveguide,
wherein the micro lens condenses the fluorescent light onto the light receiving device, and
wherein a surface of the micro lens provices the at least one reaction region.

23. The method of claim 22, wherein the providing of the light transfer portion comprises:
applying an excitation light absorbing material on an upper surface of the sample detection portion, wherein the excitation light absorbing material absorbs an excitation light and transmits a fluorescent light;
forming the excitation light absorbing waveguide by forming at least one trench in the applied excitation light absorbing material to expose the light incident surface of the sample detection portion except for the portion thereof where the light receiving device is located; and
filling a black material which absorbs the excitation light and the fluorescent light in the at least one trench to form a light blocking portion.

24. The method of claim 22, wherein the providing of the light transfer portion comprises:
applying a black material which absorbs the excitation light and the fluorescent light on an upper surface of the sample detection portion;
forming at least one trench in the applied black material to expose the light incident surface of the sample detection portion where the light receiving device is located, to form a light blocking portion; and
filling an excitation light absorbing material that absorbs the excitation light and transmits the fluorescent light in the at least one trench to form the excitation light absorbing waveguide.

25. The method of claim 22, wherein the providing of the light transfer portion comprises:
forming at least one penetration hole in a substrate;
filling a color filter material in the at least one penetration hole to from a color filter core; and
bonding the substrate and the color filter core to the light incident surface of the sample detection portion.

26. The method of claim 25, wherein the providing of the light transfer portion comprises disposing a clad layer on an inner wall of the at least one penetration hole before forming the color filter core.

27. The method of claim 22, wherein the sample detection portion comprises at least one selected from the group consisting of a photo multiplier tube, a charge coupled device and a complementary metal oxide semiconductor image sensor.

28. The method of claim 27, wherein the preparing of the sample detection portion comprises:
preparing a pre-polished sample detection portion including a photodiode portion including photodiodes and a distribution line portion disposed on a surface of the photodiode portion;
bonding a dummy substrate on a surface of the pre-polished sample detection portion where the distribution line portion is disposed; and
polishing the opposite surface of the pre-polished sample detection portion to a predetermined depth;
wherein the light transfer portion is disposed on the surface of the sample detection portion where the photodiode portion is disposed.

29. The method of claim 22, wherein the at least one light receiving device of the sample detection portion corresponds to the at least one excitation light absorbing waveguide in one of a one-to-one correspondence and a one-to-many correspondence.

30. The method of claim 22, wherein the bonding of the light transfer portion to the sample detection portion is performed in one of a wafer unit and a single chip unit.

31. The method of claim 22, further comprising disposing a cover glass at a predetermined distance from the sample reaction portion.

32. The method of claim 31, wherein the disposing of the cover glass comprises: forming a fluorescence reflection layer that reflects a fluorescent light emitted from the at least one sample on an inner surface of the cover glass.

33. The method of claim 31, wherein the disposing of the cover glass comprises providing at least one micro mirror that condenses and reflects a fluorescent light emitted from the at least one sample on the inner surface of the cover glass.

34. The method of claim 33, wherein the disposing of the at least one micro mirror comprises forming the micro mirror to be concave to reflect the fluorescent light from the at least one sample while condensing the fluorescent light incident thereto.

35. The method of claim 33, wherein the disposing of the at least one micro mirror comprises forming the micro mirror to correspond to the reaction region of the sample reaction portion in one of a one-to-one correspondence and a one-to-many correspondence.

36. The method of claim 31, wherein the disposing of the cover glass further comprises an anti-excitation light reflection layer which prevents an excitation light from being reflected on an outer surface of the cover glass.

37. A bio-material detecting apparatus using an integrated bio-chip, which includes: a sample detection portion including at least one light receiving device which detects fluorescent light; a light transfer portion disposed on a light incident surface of the sample detection portion, and which includes at least one excitation light absorbing waveguide which absorbs an excitation light for exciting samples and which transmits a fluorescent light emitted from the at least one sample; a sample reaction portion disposed on a portion corresponding to an incident end of the at least one excitation light absorbing waveguide in the light transfer portion, and including at least one reaction region on which the at least one sample is attached; and a micro lens disposed on a light incident end of the at least one excitation light absorbing waveguide, wherein the micro lens condenses the fluorescent light onto the light receiving device, wherein a surface of the micro lens provides the at least one reaction region, and wherein the sample detection portion, the light transfer portion, and the sample reaction portion are integrally coupled to each other, the bio-material detecting apparatus comprising:
- an illumination optics which illuminates excitation light to the integrated bio-chip; and
- a stage on which the integrated bio-chip is detachably installed.

* * * * *